(12) United States Patent
Carlson et al.

(10) Patent No.: US 12,191,030 B2
(45) Date of Patent: Jan. 7, 2025

(54) MEDICAL DEVICE WITH NATURAL LANGUAGE PROCESSOR

(71) Applicant: ZOLL MEDICAL CORPORATION, Chelmsford, MA (US)

(72) Inventors: Rachel H. Carlson, Falls Creek, PA (US); Shane S. Volpe, Saltsburg, PA (US); Thomas E. Kaib, North Huntingdon, PA (US); Gregory R. Frank, Mt. Lebanon, PA (US); Jason T. Whiting, Gibsonia, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 922 days.

(21) Appl. No.: 14/657,790

(22) Filed: Mar. 13, 2015

(65) Prior Publication Data

US 2016/0004831 A1 Jan. 7, 2016

Related U.S. Application Data

(60) Provisional application No. 62/025,660, filed on Jul. 17, 2014, provisional application No. 62/021,609, filed on Jul. 7, 2014.

(51) Int. Cl.
*G16H 40/63* (2018.01)
*G16H 10/20* (2018.01)

(52) U.S. Cl.
CPC ............ *G16H 40/63* (2018.01); *G16H 10/20* (2018.01)

(58) Field of Classification Search
CPC ... G06F 19/3406; G06F 19/363; G16H 40/63; G16H 10/20
See application file for complete search history.

(56) References Cited

U.S. PATENT DOCUMENTS

| 3,534,727 A | 10/1970 | Roman |
| 3,553,651 A | 1/1971 | Bird et al. |
| 4,094,310 A | 6/1978 | McEachern et al. |
| 4,136,690 A | 1/1979 | Anderson et al. |
| 4,422,459 A | 12/1983 | Simson |
| 4,458,691 A | 7/1984 | Netravali |
| 4,632,122 A | 12/1986 | Johansson et al. |

(Continued)

FOREIGN PATENT DOCUMENTS

| EP | 1642616 A2 | 4/2006 |
| EP | 1455640 B1 | 1/2008 |

(Continued)

OTHER PUBLICATIONS

PCT Search Report and Written Opinion for PCT Application No. PCT/US2015/039321, Oct. 15, 2015, 14 pages.

(Continued)

*Primary Examiner* — Gregory D. Moseley
(74) *Attorney, Agent, or Firm* — ZOLL Medical Corporation

(57) ABSTRACT

An external medical device is provided. The external medical device includes a memory and circuitry, in communication with the memory, to receive input specifying at least in part at least one prompt relating to a health survey for a patient, the at least one prompt being customized based on the patient; convert the at least one prompt to an audio representation; and perform the health survey by at least delivering to the patient the audio representation.

27 Claims, 10 Drawing Sheets

(56) References Cited

U.S. PATENT DOCUMENTS

| | | | |
|---|---|---|---|
| 4,928,690 A | 5/1990 | Heilman et al. | |
| 4,991,217 A | 2/1991 | Garrett et al. | |
| 5,000,189 A | 3/1991 | Throne et al. | |
| 5,062,834 A | 11/1991 | Gross et al. | |
| 5,078,134 A | 1/1992 | Heilman et al. | |
| 5,243,978 A | 9/1993 | Duffin, Jr. | |
| 5,330,505 A | 7/1994 | Cohen | |
| 5,342,404 A | 8/1994 | Alt et al. | |
| 5,348,008 A | 9/1994 | Bornn et al. | |
| 5,357,696 A | 10/1994 | Gray et al. | |
| 5,381,798 A | 1/1995 | Burrows | |
| 5,738,102 A | 4/1998 | Lemelson | |
| 5,741,306 A | 4/1998 | Glegyak et al. | |
| 5,758,443 A | 6/1998 | Pedrazzini | |
| 5,792,190 A | 8/1998 | Olson et al. | |
| 5,827,196 A | 10/1998 | Yeo et al. | |
| 5,887,978 A | 3/1999 | Lunghofer et al. | |
| 5,924,979 A | 7/1999 | Swedlow et al. | |
| 5,929,601 A | 7/1999 | Kaib et al. | |
| 5,944,669 A | 8/1999 | Kaib | |
| 6,016,445 A | 1/2000 | Baura | |
| 6,045,503 A | 4/2000 | Grabner et al. | |
| 6,047,203 A | 4/2000 | Sackner et al. | |
| 6,065,154 A | 5/2000 | Hulings et al. | |
| 6,097,987 A | 8/2000 | Milani | |
| 6,148,233 A | 11/2000 | Owen et al. | |
| 6,160,964 A | 12/2000 | Imoto | |
| 6,169,387 B1 | 1/2001 | Kaib | |
| 6,253,099 B1 | 6/2001 | Oskin et al. | |
| 6,280,461 B1 | 8/2001 | Glegyak et al. | |
| 6,406,426 B1 | 6/2002 | Reuss et al. | |
| 6,546,285 B1 | 4/2003 | Owen et al. | |
| 6,681,003 B2 | 1/2004 | Linder et al. | |
| 6,690,969 B2 | 2/2004 | Bystrom et al. | |
| 6,804,554 B2 | 10/2004 | Ujhelyi et al. | |
| 6,827,695 B2 | 12/2004 | Palazzolo et al. | |
| 6,865,413 B2 | 3/2005 | Halperin et al. | |
| 6,908,437 B2 | 6/2005 | Bardy | |
| 6,961,612 B2 | 11/2005 | Elghazzawi et al. | |
| 6,990,373 B2 | 1/2006 | Jayne et al. | |
| 7,074,199 B2 | 7/2006 | Halperin et al. | |
| 7,108,665 B2 | 9/2006 | Halperin et al. | |
| 7,118,542 B2 | 10/2006 | Palazzolo et al. | |
| 7,122,014 B2 | 10/2006 | Palazzolo et al. | |
| 7,149,579 B1 | 12/2006 | Koh et al. | |
| 7,220,235 B2 | 5/2007 | Geheb et al. | |
| 7,295,871 B2 | 11/2007 | Halperin et al. | |
| 7,340,296 B2 | 3/2008 | Stahmann et al. | |
| 7,453,354 B2 | 11/2008 | Reiter et al. | |
| 7,476,206 B2 | 1/2009 | Palazzolo et al. | |
| 7,488,293 B2 | 2/2009 | Marcovecchio et al. | |
| 7,712,373 B2 | 5/2010 | Nagle et al. | |
| 7,728,548 B2 | 6/2010 | Daynes et al. | |
| 7,831,303 B2 | 11/2010 | Rueter et al. | |
| 7,974,689 B2 | 7/2011 | Volpe et al. | |
| 7,991,460 B2 | 8/2011 | Fischell et al. | |
| 8,121,683 B2 | 2/2012 | Bucher et al. | |
| 8,140,154 B2 | 3/2012 | Donnelly et al. | |
| 8,369,944 B2 | 2/2013 | Macho et al. | |
| 9,283,399 B2 | 3/2016 | Donnelly et al. | |
| 2003/0004547 A1 | 1/2003 | Owen et al. | |
| 2006/0100850 A1* | 5/2006 | Lee | G06F 40/58 704/8 |
| 2007/0021979 A1* | 1/2007 | Cosentino | A61B 5/0031 705/2 |
| 2007/0232866 A1* | 10/2007 | Nephin | G06F 19/3418 600/300 |
| 2007/0276270 A1* | 11/2007 | Tran | A61B 5/0022 600/508 |
| 2009/0231124 A1 | 9/2009 | Klabunde et al. | |
| 2009/0232286 A1 | 9/2009 | Hurwitz | |
| 2009/0234410 A1 | 9/2009 | Libbus et al. | |
| 2009/0234916 A1* | 9/2009 | Cosentino | G01G 23/3742 709/217 |
| 2009/0264792 A1 | 10/2009 | Mazar | |
| 2009/0275848 A1 | 11/2009 | Brockway et al. | |
| 2009/0281394 A1 | 11/2009 | Russell et al. | |
| 2009/0287120 A1 | 11/2009 | Ferren et al. | |
| 2009/0292194 A1 | 11/2009 | Libbus et al. | |
| 2009/0295326 A1 | 12/2009 | Daynes et al. | |
| 2009/0307266 A1 | 12/2009 | Fleizach et al. | |
| 2009/0318779 A1 | 12/2009 | Tran | |
| 2010/0010559 A1 | 1/2010 | Zhang et al. | |
| 2010/0052892 A1 | 3/2010 | Allen et al. | |
| 2010/0052897 A1 | 3/2010 | Allen et al. | |
| 2010/0056881 A1 | 3/2010 | Libbus et al. | |
| 2010/0069735 A1 | 3/2010 | Berkner | |
| 2010/0076513 A1 | 3/2010 | Warren et al. | |
| 2010/0076533 A1 | 3/2010 | Dar et al. | |
| 2010/0081962 A1 | 4/2010 | Hamaguchi et al. | |
| 2010/0114243 A1 | 5/2010 | Nowak et al. | |
| 2010/0171611 A1 | 7/2010 | Gao et al. | |
| 2010/0234716 A1 | 9/2010 | Engel | |
| 2010/0241181 A1 | 9/2010 | Savage et al. | |
| 2010/0295674 A1 | 11/2010 | Hsieh et al. | |
| 2010/0298899 A1 | 11/2010 | Donnelly et al. | |
| 2010/0312297 A1 | 12/2010 | Volpe et al. | |
| 2011/0015533 A1 | 1/2011 | Cox et al. | |
| 2011/0022105 A9 | 1/2011 | Owen et al. | |
| 2011/0093840 A1 | 4/2011 | Pynenburg et al. | |
| 2011/0098765 A1 | 4/2011 | Patel | |
| 2011/0170692 A1 | 7/2011 | Konrad et al. | |
| 2011/0172550 A1 | 7/2011 | Martin et al. | |
| 2011/0288604 A1 | 11/2011 | Kaib et al. | |
| 2011/0288605 A1 | 11/2011 | Kaib et al. | |
| 2012/0053479 A1 | 3/2012 | Hopenfeld | |
| 2013/0073306 A1* | 3/2013 | Shlain | G06Q 10/06 705/2 |
| 2013/0144355 A1 | 6/2013 | Macho et al. | |
| 2014/0025131 A1 | 1/2014 | Sullivan et al. | |
| 2014/0046391 A1* | 2/2014 | Cowan | A61N 1/3993 607/5 |
| 2014/0245161 A1* | 8/2014 | Yuen | G06F 3/011 715/736 |
| 2017/0293729 A1* | 10/2017 | Movva | A61B 5/0022 |

FOREIGN PATENT DOCUMENTS

| | | |
|---|---|---|
| EP | 1720446 B1 | 7/2010 |
| JP | 2002-514107 A | 5/2002 |
| JP | 2002200059 A | 7/2002 |
| JP | 2009-521865 A | 6/2009 |
| WO | 2004067083 A2 | 8/2004 |
| WO | 2004078259 A1 | 9/2004 |
| WO | 2005082454 A1 | 9/2005 |
| WO | 2006050325 A2 | 5/2006 |
| WO | 2007019325 A2 | 2/2007 |
| WO | 2009034506 A1 | 3/2009 |
| WO | 2010025432 A1 | 3/2010 |
| WO | 2010077997 A2 | 7/2010 |
| WO | 2012174659 A1 | 12/2012 |
| WO | 2013130957 A2 | 9/2013 |

OTHER PUBLICATIONS

American Journal of Respiratory and Critical Care Medicine, vol. 166, pp. 111-117 (2002). American Thoracic Society, ATS Statement Guidelines for the Six-Minute Walk Test, available at http://ajrccm.atsjournals.org/cgi/content/full/166/1/111.

DeBock et al., "Captopril treatment of chronic heart failure in the very old," J. Gerontol. (1994) 49: M148-M152.

O'Keeffe et al., "Reproducability and responsiveness of quality of the assessment and six minute walk test in elderly heart failure patients," Heart (1998) 80: 377-382.

Association for the Advancement of Medical Instrumentation, ANSI/AAMI DF80:2003 Medical Electrical Equipment—Part 2-4: Particular Requirements for the Safety of Cardiac Defibrillators (includ-

(56) References Cited

OTHER PUBLICATIONS ing Automated External Defibrillators) 2004, ISBN 1-57020-210-9; abstract; p. vi; p. 50, section 107.1.2.

* cited by examiner

| Alerts | Wear Time | All Recordings | Trends | Trend Setup |
| Setup Info | Health Survey Setup | Walk Test Setup | | |

Schedule Health Survey

○ Disable Feature  ● Daily  ○ Weekly

Number of Iterations: ● Indefinitely
○ Enter Number ☐

Populate from prescribers lists: [▽]   List Manager

Select questions to ask this patient:
☑ How many pillows did you sleep on last night?
☑ Has your weight changed from yesterday?
☑ How much activity have you averaged in the past few days?
☑ Have you felt dizzy?
☑ Are you feeling fatigued?
☑ Are you having difficulty climbing the stairs?
☑ Have you felt your heart racing?
☑ Have you felt your heart beating irregularly?
☑ Are you short of breath?
☑ Do you have swelling in your ankles and legs?
☑ Have you had any chest pain?
☑ Have you missed any medications?

[Save]

FIG. 7

| Alerts | Wear Time | All Recordings | Trends | Trend Setup | | |
|---|---|---|---|---|---|---|
| Summary | | Body Position | | Health Survey Review | Walk Test Review | |

Health Survey Results Review
Date Performed: 2014-05-21 06:43:30 AM ⌄  Previous
Additional Health Surveys:
Number of Health Surveys performed by this patient: 11

Trend Data

Results

| Question | Patient Response |
|---|---|
| How many pillows did you sleep on last night? | 1 |
| Has your weight changed from yesterday? | No change |
| How much activity have you averaged in the past few days? | 3-4 hours/day |
| Have you felt dizzy? | No/not applicable |
| Are you feeling fatigued? | No/not applicable |
| Are you having difficulty climbing the stairs? | No/not applicable |
| Have you felt your heart racing? | No/not applicable |
| Have you felt your heart beating irregularly? | No change |
| Are you short of breath? | No/not applicable |
| Do you have swelling in your ankles and legs? | No/not applicable |
| Have you had any chest pain? | No/not applicable |
| Have you missed any medications? | Yes |

FIG. 8

MEDICAL DEVICE WITH NATURAL LANGUAGE PROCESSOR

RELATED APPLICATIONS

The present application claims priority under 35 U.S.C. § 119(e) to U.S. Provisional Application Ser. No. 62/025,660, titled "Wearable Defibrillator," filed on Jul. 17, 2014, which is hereby incorporated herein by reference in its entirety. The present application claims priority under 35 U.S.C. § 119(e) to U.S. Provisional Application Ser. No. 62/021,609, titled "Wearable Defibrillator," filed on Jul. 7, 2014, which is hereby incorporated herein by reference in its entirety.

BACKGROUND

Technical Field

This disclosure relates to medical devices, and more particularly to medical devices that include user interfaces.

Discussion

Modern medical devices embody a variety of user interface components. These user interface components may include both input and output components. Examples of components that generate sensory output include visual displays, speakers, and electromechanical vibrators. Examples of components that receive input include touch screens, buttons, and switches. In combination, these inputs and outputs enable users, such as patients, care providers, and others, to setup and operate medical devices to the benefit of patients.

SUMMARY

Some aspects and examples disclosed herein implement a user interface in which communications are exchanged between a medical device and a user in a natural language (e.g., spoken/verbal communication in any language, sign language for the hearing impaired, and/or Braille for the visually impaired). For example, medical devices in accord with some examples store data descriptive of one or more prompts to be provided to a user to initiate a response from the user. Each of the one or more prompts may include one or more words, phrases, or sentences rendered as one or more declaratives, interrogatories, imperatives, or exclamations. The data descriptive of the one or more prompts may be stored as encoded data, such as text, that is decoded by a natural language processing component. In some examples, the natural language processing component renders the one or more prompts as audio prompts via a speaker or some other audio or tactile output device. In some examples, the natural language processing component renders the one or more prompts as sign language via a display, such as a touch screen.

In some examples, sets of these prompts are grouped together to form customized health surveys, instructions, and training materials. The training materials may cover normal usage of the external medical device and maintenance topics, such as battery replacement, garment care, assembly/attachment of components, and the like. In these examples, the prompts included in a customized health survey may be selected by a user in view of the medical history and current condition of a patient. In some examples, prompts included in training materials and instructions may be selected by a user in view of an operational issue with the medical device (e.g., maintenance that needs to be performed) or an inability of a user to accomplish some objective regarding the medical device (e.g., the user has been unable to silence an alarm emitted by the medical device).

In some examples, an external medical device is provided. The external medical device includes a memory and circuitry, in communication with the memory, to receive input specifying at least in part at least one prompt relating to a health survey for a patient, the at least one prompt being customized based on the patient; convert the at least one prompt to an audio representation; and perform the health survey by at least delivering to the patient the audio representation.

In the external medical device, the circuitry may include circuitry to provide a user interface including a set of selectable prompts directed to a condition of the patient. The circuitry may include circuitry to determine, based on the input, a time period for the health survey comprising the at least one prompt relating to the health survey; and schedule the health survey for the patient during the time period. The circuitry may include circuitry to determine the time period based on an operating mode of the device. The circuitry may include circuitry to determine the time period based on an operating mode of the device, wherein the operating mode includes a health survey mode and the time period based on the health survey mode is as soon as possible.

In the external medical device, the input may specify the target time period. The input may omit the target time period and the circuitry may include circuitry to store the target time period as a default time period. The circuitry may include circuitry to output the at least one audio representation during the target time period. The circuitry may include circuitry to receive at least one response to the at least one prompt, record the at least one response, determine results based on the at least one response, and provide the results to an external entity via the user interface. The circuitry to receive the at least one response may include circuitry to process audio representations. The circuitry may includes circuitry to receive at least one response to the at least one prompt and output an audio representation of at least one other prompt based on the at least one prompt and the at least one response.

In the external medical device, the at least one prompt may include a plurality of prompts. The circuitry may include a global positioning system (GPS) receiver and circuitry to receive a location identifier from the GPS receiver, to determine a language associated with the location, and the audio representation is converted to the language. The target time period may include a reoccurring time period. The circuitry may include circuitry to receive at least one response to the at least one prompt, identify the at least one response as at least one addressable response, and address the response.

The external medical device may further include a cross-reference stored in the memory. The cross-reference may include associations between response types and addresses for target recipients. The circuitry of the external medical device may include circuitry to receive at least one response to the at least one prompt, to identify at least one response type of the at least one response, to identify at least one address for at least one target recipient from the cross-reference using the at least one response type, and to transmit at least one notification to the at least one target recipient.

In some examples, the cross-reference may include associations between response types and addresses for target recipients. The circuitry of the external medical device may include circuitry to receive at least one response to the at least one prompt, to identify at least one response type of the at least one response, to identify at least one address for at least one target recipient from the cross-reference using the at least one response type, and to transmit at least one notification to the at least one target recipient, the target recipient being a device associated with at least one of a healthcare provider, support provider, and care taker and the notification including an natural language representation of at least one of a name of the patient, a location of the patient, a condition of the patient, and the at least one response.

In some examples, the cross-reference may include associations between response types and priorities for subsequent actions. The circuitry of the external medical device may include circuitry to receive at least one response to the at least one prompt, to identify at least one response type of the at least one response, to identify at least one priority from the cross-reference using the at least one response type, and to transmit at least one notification with the at least one priority.

In some examples, an external medical device is provided. The external medical device includes a memory and circuitry, in communication with the memory, to monitor one or more indicators of a patient's health, detect a potential health condition based on the one or more indicators, identify at least one prompt associated with the potential condition, generate audio output conveying the at least one prompt, receive a response to the at least one prompt, and adjust a configurable parameter of the external medical device based on the at least one prompt and the response.

In the external medical device, the one or more indicators may include one or more indicators of cardiac function, respiratory function, and vocal function. The configurable parameter may define a course of treatment executed by the external medical device to treat the potential health condition. The potential health condition may include at least one of ventricular tachycardia, ventricular fibrillation, bradycardia, and asystole.

In some examples a system is provided. The system includes a computer system including a memory and circuitry, in communication with the memory, to provide a user interface including a set of selectable prompts directed to a condition of an external medical device, each selectable prompt of the set of selectable prompts corresponding to text articulating the selectable prompt; receive input selecting at least one prompt from the set of selectable prompts to include in a training message directed to the condition; and transmit the training message to the external medical device. The system also includes the external medical device. The external medical device includes a memory and circuitry, in communication with the memory, to receive the training message, convert the text corresponding to the at least one prompt to at least one natural language representation of the at least one prompt, and output the at least one natural language representation. In the system, the condition may include a low battery and the at least one prompt may include a request to change the battery.

It is appreciated that various examples described herein provide a host of advantages over conventional technology. These advantages include clinical flexibility, the ability to upgrade devices "on the fly" (e.g., without requiring physical access to the device by technicians), and the ability to rapidly deploy devices to new markets (e.g., without requiring loading of different audio files, which may consume substantial storage).

Still other aspects and advantages of the examples disclosed herein are discussed in detail below. Moreover, it is to be understood that both the foregoing information and the following detailed description are merely illustrative examples of various aspects, and are intended to provide an overview or framework for understanding the nature and character of the claimed subject matter. Any example disclosed herein may be combined with any other example. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings:

FIG. 7 is an illustration of one example of a health survey configuration screen;

FIG. 8 is an illustration of one example of a health survey results screen;

DETAILED DESCRIPTION

Figure 1:
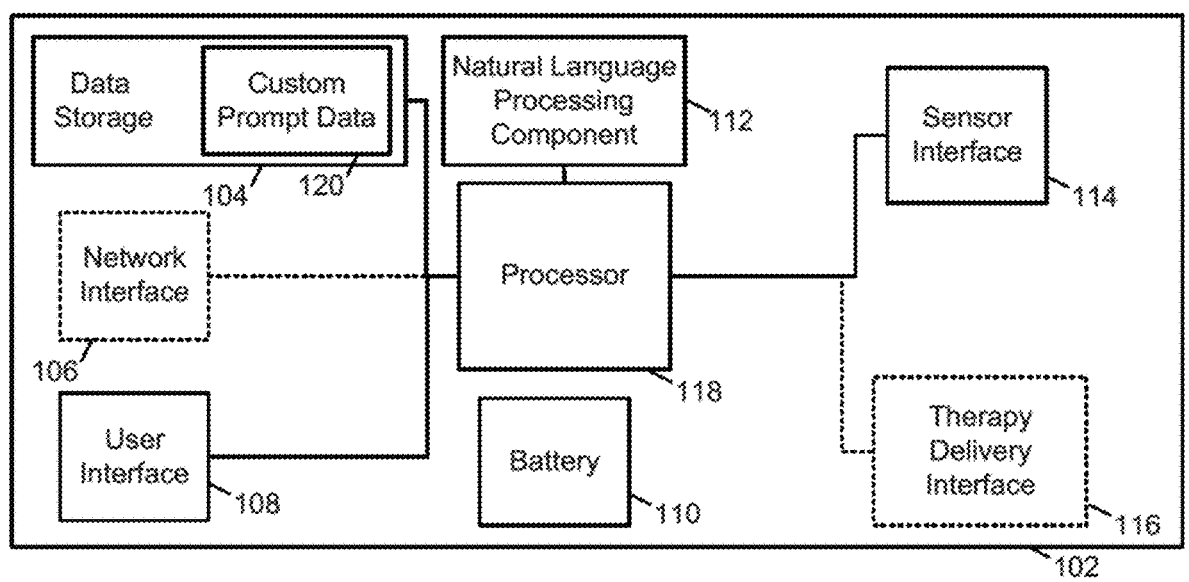
FIG. 1 is a functional schematic one example of an external medical device controller.

Medical devices in accord with various examples disclosed herein use natural language to interact with external entities, such as patients being monitored by the medical devices, other users of the medical devices such as health care professionals and patient service representatives, and third parties, such as bystanders. For instance, according to some examples, an external medical device includes a natural language processing component configured to read information descriptive of one or more prompts and articulate the one or more prompts in a natural language, such as through audio output or visual gestures (e.g., sign language). In some examples, the natural language processing component is also configured to detect responses in a natural language, e.g., spoken audio, and convert the natural language into encoded data, such as human-readable text, for storage and further processing. Further, in some examples, the natural language processing component is configured to analyze the responses, address the responses by, for example, altering the operation of the external medical device, and report responses to the prompts. In various examples, prompts may be defined by a user of the system and, accordingly, include custom prompts.

Some examples use this natural language processing capability to enhance patient care. For instance, according one example, a medical device is configured to receive information descriptive of a health survey customized for one or more target patients. This health survey information may identify one or more prompts for information specifically selected for the one or more target patients. In some examples, the medical device is configured execute the health survey by issuing the one or more identified prompts and recording any responses received to the prompts.

In some examples, the medical device is configured to analyze the responses and identify whether any of the responses should be addressed. In these examples, the medical device is further configured to address the responses according to custom prompt information stored in the medical device. For example, if a response indicates that the patient requires assistance, the medical device may contact an external entity identified in the custom prompt information to request assistance on behalf of the patient.

In some examples, the medical device is configured to receive information descriptive of one or more instructions or more comprehensive training (e.g., comprising a set of instructions as a self-contained training module) customized for one or more target recipients. This training information may identify one or more prompts for information or action specifically selected for the one or more target recipients. For example, the training information may be directed to an activity associated with the medical device that a patient is having difficulty in performing. In some examples, the medical device is configured to provide the instructions or training by issuing the one or more identified prompts through natural language output, such as audio output.

For example, any of the medical devices disclosed herein may be non-invasive or ambulatory. As used herein, the term non-invasive is in contrast to invasive devices, such as implantable medical devices. For example, non-invasive medical devices disclosed herein can include wearable medical devices. The term ambulatory means that the device is capable of and designed for moving with the patient.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Example Medical Device Controller

Various examples disclosed herein use natural language processing to communicate prompts in a natural language and receive verbal and/or non-verbal responses through textual input (e.g., user selects one or more predefined responses or types in a response via a user interface) or natural language input (e.g., user speaks desired response or speaks selection of one or more predefined responses). Target recipients for these prompts may include patients being monitored by the external medical device, care givers for the patient, or third party bystanders, among others. FIG. 1 illustrates an external medical device controller 102 in accord with some examples. The external medical device controller 102 may be included in any of a variety of external medical devices including defibrillators, monitors, CPR systems, pacing devices, and other medical devices. More specific examples of medical devices including a controller in accord with the external medical device controller 102 are described further below with reference to FIGS. 3-5. In these examples, the external medical device controller 102 is configured for use in a wearable defibrillator or an Automated External Defibrillator (AED).

As shown in FIG. 1, the external medical device controller 102 includes at least one processor 118, a sensor interface 114, a natural language processing component 112, a therapy delivery interface 116, data storage 104, a network interface 106, a user interface 108, and a battery 110. The processor 118 can be implemented using a variety of commercially available processors or other circuitry. Specific examples of the processor 118 are described further below. The data storage 104 includes custom prompt data 120. The sensor interface 114 can include an acoustic signal processing component, an electrode signal processing component, and motion signal processing component, among other signal processing components. In some implementations, components such as natural language processing component 112 and sensor interface 114 can be at least partially implemented within the processor 118. In some implementations, the components can be implemented in circuitry that is separate from processor 118. For example, in one example the natural language processing component 112 includes voice circuitry in communication with a memory of the controller 102 and configured to perform the one or more processes as described herein. As referred to herein, "circuitry" may include controllers, processors, transistors, integrated circuits, microprocessors, and the like. As such, some forms of circuitry can be configured by various software components to execute particular features and functions. As discussed further below, these software components may be stored in the data storage 104 or in an on-board storage element in processor 118.

In some examples in accord with FIG. 1, the battery 110 may be a rechargeable 3 cell 2200 mAh lithium ion battery pack that provides electrical power to the other device components with at least 24 hour runtime between charges. It is appreciated that the battery capacity, runtime, and type (e.g., lithium ion, nickel-cadmium, or nickel-metal hydride) may be changed to best fit the specific application of the medical device controller 102.

According to the example illustrated in FIG. 1, the processor 118 can be coupled to and in data communication with one or more of the sensor interface 114, the therapy delivery interface 116, the data storage 104, the network interface 106, and the user interface 108. In some examples, the processor 118 performs a series of instructions that result in manipulated data which are stored in and retrieved from the data storage 104. According to a variety of examples, the processor 118 is a commercially available processor such as a processor manufactured by Texas Instruments, Intel, AMD, Sun, IBM, Motorola, Freescale, and ARM Holdings. However, the processor 118 may be any type of processor, multiprocessor or controller, whether commercially available or specially manufactured. For instance, according to one example, the processor 118 may include a power conserving processor arrangement as described in U.S. Pat. No. 8,904,214, titled SYSTEM AND METHOD FOR CONSERVING POWER IN A MEDICAL DEVICE, issued Dec. 2, 2014, which is hereby incorporated herein by reference in its entirety. In one example, the processor 118 is an Intel® PXA270.

In addition, in several examples, the processor 118 is configured to execute a conventional operating system. The operating system may provide platform services to application software, such as some examples of the natural language processing component 112 which is discussed further below. These platform services may include inter-process and network communication, file system management and standard database manipulation. One or more of many operating systems may be used, and examples are not limited to any particular operating system or operating system characteristic. For instance, in some examples, the processor 118 may be configured to execute a real-time operating system (RTOS), such as RTLinux, or a non-real time operating system, such as BSD or GNU/Linux.

In various examples, the sensor interface 114 is configured to couple to and receive acoustic signals from an acoustic sensor. Similarly, the sensor interface 114 may be configured to couple to and receive electrode signals from one or more electrodes. These electrodes may comprise any of a variety of commercially available electrodes, some examples of which are described further below. As illustrated in FIG. 1, in some examples, the natural language processing component 112 can be coupled with and receive processed acoustic data from the sensor interface 114 via the processor 118. Similarly, the natural language processing component 112 may be coupled with and receive response data from the user interface 108 or the sensor interface 114 via the processor 118. In various examples, the response data is descriptive of verbal responses to one or more communicated prompts.

Natural Language Processing Component

According to one example illustrated by FIG. 1, the natural language processing component 112 is configured to receive an identifier of text or other encoded data specifying at least one prompt to be communicated to a patient monitored by the external medical device. As discussed in more detail below, the natural language processing component 112 may perform a natural language generation process to convert the received data to a prompt or an instruction. For example, prompts can take the form of questions in a health survey, instruction and training messages, or device maintenance-related topics. In various examples, the natural language processing component 112 is configured to generate an output conveying at least one prompt to the user (e.g., a patient), and receive a response to the at least one prompt. For example, as described in detail below, the output prompt may be a spoken question in a language of the user, and the user's response may be received via a microphone assembly in the user interface 108 and processed by the natural language processing component 112. In one example, the prompt can be communicated to the patient during a predetermined target time period or a default time period. The time period may be configured in the form of a single discrete time or a time range, and may include non-reoccurring or reoccurring time periods.

In one example, the external medical device controller 102 is configured to determine the time period for delivering the health survey based on an operating mode of an associated external medical device. The device may include one or more predetermined operating modes, such as a health survey mode. In various examples, each of the one or more operating modes controls the behavior of the device its operation. Modes may be activated by default or through user interaction with the user interface 108 that causes the user interface 108 to store a value in a configurable parameter that defines the operating mode. For example, in one implementation the external medical device controller 102 is configured to determine that the operating mode of the device is presently the health survey mode by referencing the value of the configurable parameter and to cause the health survey to be automatically performed during the health survey mode. As described above, this can include automatically communicating a prompt at a determined target time period (e.g., as soon as possible).

Similarly, in some examples, the external medical device controller 102 includes additional modes in which the natural language processing component 112 interacts with users. For instance, in some examples the external medical device controller 102 implements a maintenance mode in which the external medical device controller 102 issues prompts to the user to aid the user in performing maintenance functions such as battery replacement, component assembly, garment care, and the like. Moreover, in some examples, the external medical device controller 102 implements a training mode in which the external medical device controller 102 issues prompts to the user to train the user on how to operate the external medical device in which the external medical device controller 102 is housed.

The natural language processing component 112 may also perform natural language understanding to convert the user's response to a binary representation of a human readable symbol, such as text, for, e.g., storage and later retrieval. In various other examples, the natural language component 112 is configured to receive a transmission including custom prompt data specifying at least one message and convert the data to an audio representation of the at least one message. For example, a doctor may customize one or more prompts based on a patient's underlying condition. The doctor may customize prompts by, e.g., speaking his/her questions into the device microphone. The doctor may be given audio or visual feedback regarding the spoken question, e.g., human readable text rendering of the question can be displayed to the doctor, or alternatively the doctor's recorded question may be played back to him. The doctor may then accept or reject the recording.

In various examples, the audio output, or audio representation, may be output by the user interface 108 and communicated to the patient monitored by the external medical device. Processes performed by the natural language processing component 112 are described in detail below with reference to FIG. 10.

In various examples, the natural language processing component 112 is configured to modify and adjust prompts based on language based parameters, location information associated with an external medical device, or the response received to at least one prompt. Language based parameters may indicate primary language, dialect, spoken word, sign language, gender of voice, speed of diction, accent, and vocabulary/word choice. Language based parameters may be received from a user of the external medical controller 102, such as the patient, through one or more interfaces such as the user interface 108. Accordingly, in one or more examples, the external medical device controller 102 includes a configurable parameter storing a value that specifies a one or more languages in which the external medical device controller 102 communicates. By setting this configurable parameter to one or more predefined values, a user may manually select one or more languages through which the external medical device controller 102 communicates prompts Location information may include information descriptive of a geographic location, such as an address, a state, a country, etc. In one example, location information may be received through antennas integrated with or coupled to the network interface 106, and consequently coupled to the processor 118. For example, the one or more antennas may receive GPS signals from satellites. In various examples, the natural language processing component 112 can also determine language based parameters from a response to the prompt. For example, the natural language processing component 112 may perform natural language understanding to determine that the response to a prompt is in a particular dialect. In further examples, the natural language processing component 112 may determine a natural language associated with a location identified by received GPS signals. Accordingly, various examples of the natural language processing component 112 modify and adjust prompts to accommodate a particular patient. In various examples, this includes translating a prompt to a language that the patient has spoken or is known to understand. While in some examples this may include spoken language, in further examples this may include non-spoken languages, such as sign language. While discussed herein in the context of a single verbal or non-verbal language, various examples of the controller 102 may communicate, modify, and adjust prompts in a plurality of natural languages. For example, responsive to receiving a GPS signal, the controller 102 can determine that more than one natural language is associated with the location corresponding to the GPS signal. Accordingly, prompts can be tailored to each language associated with the particular location. For example, several translations of a single prompt may be communicated. Furthermore, prompts may be communicated in both verbal and non-verbal languages (e.g., English and American sign language or ASL).

According to one example illustrated by FIG. 1, the natural language processing component 112 may be further configured to detect the rhyme, meter, pitch, or pace of expression, or respiration of the patient to aid in determining the patient's status. The natural language processing component 112 may include circuitry configured to detect speech or respiration exhibited in patient responses and to identify a condition based on a comparison of the detected speech or respiration and a benchmark. In one example, the circuitry is coupled with and receives response data from the user interface 108 via the processor 118. In this example, the circuitry measures and compares an envelope of received response data to a benchmark specifying characteristics of breathing or speech (e.g., breath rate, volume patterns, etc.) associated with a particular health condition. In some examples, the circuitry may further compare processed acoustic data and processed electrode data to benchmarks to identify the presence or absence of particular health conditions. Identified breathing or speech may additionally be tracked to determine trends in patient's speech or respiration. Detecting and evaluating breathing or speech patterns, permits the natural language processing component 112 to diagnose and track health conditions such as congestive heart failure, or other symptoms associated with cardiac dysfunction. In some examples, the medical device controller 102 can adjust a device parameter in response to the detected speech and/or respiration patterns (e.g., audible labored breathing) of the patient. For example, in addressing a patient's response to a custom prompt, the medical device controller 102 may detect one or more speech and/or respiration patterns that indicate an underlying health condition and alter a course of treatment or perform some other action. For example, the controller 102 may delay or expedite the administration of pacing pulses and/or defibrillation treatment, adjust a configurable operational parameter of the external medical device, prompt a third party to take action via a natural language prompt such as requesting emergency back-up, and/or report the event and information regarding the patient, such as location, identity, and vital signs).

For example, if the patient is experiencing labored breathing during an activity (e.g., a device-guided six-minute walk test), the controller 102 can use one or more detected speech patterns to suggest to the patient, caregiver, or other user, that the patient should slow down or stop the activity. In some implementations, the controller 102 can combine the detected speech patterns with other sensed information (e.g., using the acoustic signal processing component in sensor interface 114) and determine an appropriate course of action based on the combination of the detected speech patterns and other sensed information. For example, the controller 102 may determine that the patient's breathing is labored through one or more speech patterns in the patient's response to a prompt and, if lung sounds detected by acoustic signal processing component confirm the determination, the controller 102 may advice the patient to stop performing the activity. In other examples, a heart rate detector may provide additional correlating information, e.g., detecting if patient's heart rate exceeds a threshold (such as 150 bpm).

The natural language processing component 112 may be implemented using hardware or a combination of hardware and software. For instance, in one example, the natural language processing component 112 is implemented as a software component that is executed by the processor 118. In this example, the instructions included in the natural language processing component 112 program the processor to derive meaning from human (natural) language, such as text or a response to a prompt. For instance, this may include converting a computer based representation into a natural language representation (i.e., natural language generation) or converting received natural language into a computer based representation (i.e., natural language understanding). In various examples the natural language processing component 112 includes a lexicon of language, a parser, and grammar rules. Additionally, the natural language processing component 112 may reference a semantic theory to guide natural language understanding processes executed by the natural language processing component 112. In various examples, a semantic theory characterizes a sentence based on its structure and context.

During natural language understanding, the natural language processing component 112 first executes a process of decomposing the response into phonemes. This may be performed by the parser. Phonemes include any of the units of sound in a language that distinguish one word from another. For example, the English language has roughly 40 phonemes. Each phoneme is then identified in the lexicon of language and assessed according to the grammar rules and semantic theory. Accordingly, phonemes are matched to spoken words based on the particular rules and theory. Alternatively, the natural language processing component 112 can be configured to perform statistical modeling using probability and mathematical functions to determine the most likely match between phonemes and words. For example, this may include the Hidden Markov Model or neural networks. Statistical modeling accommodates for accents, dialects, and mannerisms that may change between users. Responsive to the matching phonemes to spoken words, the sentence may be reconstructed in a computer based representation.

In contrast, during natural language generation phonemes are assigned to text. In various examples the natural language processing component 112 includes a store of voice references including all of the phonemes and voice references for a given language. Initially, the text next goes through a process of tokenization. This process divides the text into basic language units such as words or morphemes. This may be performed by the parser, for example. A morpheme is the smallest grammatical unit of a language. Divisions are generally made using separators such as punctuation marks and spaces in the text. The natural language processing component 112 then performs one or more processes that assign a phonetic transcription to the text to reconstruct each word. This process may be referred to as text-to-phoneme processing. Grammatical and syntactic analysis based on at least the grammar rules and semantic theory enables the natural language processing component to reconstruct the sentence and output an audio waveform.

As discussed above, various examples of the natural language processing component 112 may perform speech synthesis processes that convert custom prompts in a text format to one or more verbal prompts (e.g., artificial speech). Accordingly, the natural language processing component 112 of one example can include a speech synthesizer, such as a text-to-speech converter that converts normal language text into speech. The text-to-speech converter generates synthesized speech by referencing a database of stored speech and linking together individual segments of recorded speech (e.g., phonemes) to construct words and sentences. In various implementations the text-to-speech converter is implemented in a hardware product. For example, the text-to-speech converter may include the Textspeak TTS-EM offered by TextSpeak of Westport, CT or the Epson S1V30120F01A100, offered by EPSON® of Long Beach, CA. In other examples, the text-to-speech converter is implemented in a software product. As described above with reference to the natural language processing component 112 of FIG. 1, various examples of the text-to-speech converter convert the raw text (e.g., custom prompts) to the equivalent of written words (i.e, tokenization). Phonetic transcriptions are then assigned to each word (i.e., text-to-phoneme). The text-to-speech converter then divides the text into phrases, clauses, and sentences and converts the resulting sentence into sound (i.e., synthesization). Often this includes the computation of pitch contour and duration of particular phonemes in the resulting sentence.

In some examples, the natural language processing component 112 is configured to identify at least one response type of a response received and identify at least one address for a target recipient associated with the response type in a cross-reference stored in memory. The cross-reference may include associations between a response type and one or more addresses for one or more target recipients. The natural language processing component 112 may be configured to transmit at least one notification to the target recipient based on an identified address. These notifications may be communicated, for instance, via network interface 106. In one example, the target recipient includes a device associated with a healthcare provider, care taker, or support personnel, and the notification includes a natural language representation of at least a name of a patient, a location of the patient, a condition of the patient, or the response. In a further example, the natural language processing component 112 may identify a priority from a cross-reference based on the response type, and transmit the associated notification with the priority identified.

As described above, the custom prompt data 120 includes identifiers of previously defined prompts, definitions of new prompts, identifiers of previously defined target events that trigger prompts, definitions of new target events that trigger prompts, identifiers of previously defined responses to be addressed, definitions of new responses to be addressed, identifiers of previously defined actions to be taken in addressing responses, and definitions of new actions to be taken in addressing responses. More particularly, according to the illustrated example, the custom prompt data 120 includes at least one prompt associated with a potential health condition of the patient. For example, the custom prompt data 120 may include a series of prompts, such as a survey of questions or periodic condition status questions which may include, for example: "Are your legs swelling?"; "Are you having breathing difficulties?"; "Have you experienced a gain in weight?"; and "Are you sitting up to sleep?". Additional survey questions that may be stored in custom prompt data 120 are discussed further below with reference to FIG. 5 and a listing of prompts 706. Various other questions relating to symptoms of health conditions may also be used in addition to or in place of such survey questions.

The custom prompt data 120 may also include one or more cross-references configured by the custom prompt interface described further below. As used herein, cross-references may consist of a queryable association between one or more identifiers and include a look-up table, hierarchical database, relational database, object oriented database, or the like.

Diagnostic Information Communications

In addition to the examples discussed above, in various examples the natural language processing component 112 may cause the controller 102 to communicate one or more system diagnostics to the user or patient. Communication may be through one or more interfaces, such as the user interface 108. System diagnostics may include any message conveying a diagnosed error in the controller 102 or an associated external medical device. In one example, system diagnostics are communicated responsive to user selection of customer support indicator in the user interface 108. Accordingly, when communication between the external medical device controller 102 and a healthcare provider system is compromised, (e.g., network interface 106 is unable to communicate with the healthcare provider system) communication of the system diagnostics to the user permits the user to convey the diagnostics to the healthcare provider system or a user associated therewith. For example, the user may use a personal mobile device, such as a smart phone, to relay the diagnostics to the healthcare provider system or the associated user.

Example Implementations of Components

In other examples, the natural language processing component 112 may be an application-specific integrated circuit (ASIC) that is coupled to the processor 118 and tailored to derive meaning from natural language. For example, the natural language processing component 112 may include circuitry to render one or more prompts as audio prompts via the user interface 108. Thus, examples of the natural language processing component 112 are not limited to a particular hardware or software implementation.

In some examples, the components disclosed herein, such as the natural language processing component 112, may read parameters that affect the functions performed by the components. These parameters may be physically stored in any form of suitable memory including volatile memory, such as RAM, or nonvolatile memory, such as a flash memory or magnetic hard drive. In addition, the parameters may be logically stored in a propriety data structure, such as a database or file defined by a user mode application, or in a commonly shared data structure, such as an application registry that is defined by an operating system. In addition, some examples provide for both system and user interfaces that allow external entities to modify the parameters and thereby configure the behavior of the components.

The data storage 104 includes a computer readable and writeable nonvolatile data storage medium configured to store non-transitory instructions and data. In addition, the data storage 104 includes processor memory that stores data during operation of the processor 118. In some examples, the processor memory includes a relatively high performance, volatile, random access memory such as dynamic random access memory (DRAM), static memory (SRAM) or synchronous DRAM. However, the processor memory may include any device for storing data, such as a non-volatile memory, with sufficient throughput and storage capacity to support the functions described herein. According to several examples, the processor 118 causes data to be read from the nonvolatile data storage medium into the processor memory prior to processing the data. In these examples, the processor 118 copies the data from the processor memory to the non-volatile storage medium after processing is complete. A variety of components may manage data movement between the non-volatile storage medium and the processor memory and examples are not limited to particular data management components. Further, examples are not limited to a particular memory, memory system, or data storage system.

The instructions stored on the data storage 104 may include executable programs or other code that can be executed by the processor 118. The instructions may be persistently stored as encoded signals, and the instructions may cause the processor 118 to perform the functions described herein. The data storage 104 also may include information that is recorded, on or in, the medium, and this information may be processed by the processor 118 during execution of instructions. The medium may, for example, be optical disk, magnetic disk or flash memory, among others, and may be permanently affixed to, or removable from, the medical device controller 102.

The data storage 104 may also include sensor data such as such as ECG signal data, interpretations of the ECG signal data (e.g., heartbeats), analog heart sounds, analog breath sounds, analog motion data, acoustic signals, electrode signals, motion signals, processed motion data, processed acoustic data, and processed electrode data. Sensor data may be analyzed by one or more system components to detect the occurrence of a medical condition, such as a cardiac arrhythmia.

As illustrated in FIG. 1, the natural language processing component 112 and the custom prompt data 120 are separate components. However, in some examples, the natural language processing component 112 and the custom prompt data 120 may be combined into a single component or re-organized so that a portion of the data included in the natural language processing component 112, such as executable code, resides in the custom prompt data 120, or vice versa. Such variations in these and the other components illustrated in FIG. 1 are intended to be within the scope of the examples disclosed herein.

The custom prompt data 120 may be stored in any logical construction capable of storing information on a computer readable medium including, among other structures, flat files, indexed files, hierarchical databases, relational databases or object oriented databases. These data structures may be specifically configured to conserve storage space or increase data exchange performance. In addition, various examples organize the custom prompt data 120 into particularized and, in some cases, unique structures to perform the functions disclosed herein. In these examples, the data structures are sized and arranged to store values for particular types of data, such as integers, floating point numbers, character strings, arrays, linked lists, and the like.

As shown in FIG. 1, the external medical device controller 102 includes several system interface components 106, 114, and 116. Each of these system interface components is configured to exchange (i.e. send or receive) data with one or more specialized devices that may be located within the housing of the medical device controller 102 or elsewhere. The components used by the interfaces 106, 114, and 116 may include hardware components, software components, or a combination of both. Within each interface, these components physically and logically couple the medical device controller 102 to the specialized devices. This physical and logical coupling enables the medical device controller 102 to communicate with and, in some examples, power or control the operation of the specialized devices. These specialized devices may include physiological sensors, therapy delivery devices, and computer networking devices.

According to various examples, the hardware and software components of the interfaces 106, 114, and 116 implement a variety of coupling and communication techniques. In some examples, the interfaces 106, 114, and 116 use leads, cables or other wired connectors as conduits to exchange data between the medical device controller 102 and specialized devices. In some examples, the interfaces 106, 114, and 116 communicate with specialized devices using wireless technologies such as radio frequency, infrared technology, and body area network (BAN) technology. The software components included in the interfaces 106, 114, and 116 enable the processor 118 to communicate with specialized devices. These software components may include elements such as objects, executable code, and populated data structures. Together, these software components provide software interfaces through which the processor 118 can exchange information with specialized devices. Moreover, in at least some examples where one or more specialized devices communicate using analog signals, the interfaces 106, 114, and 116 further include components configured to convert analog information into digital information, and vice versa, to enable the processor 118 to communicate with specialized devices.

As discussed above, the system interface components 106, 114, and 116 shown in FIG. 1 support different types of specialized devices. For instance, the components of the sensor interface 114 couple the processor 118 to one or more physiological sensors such as a body temperature sensors, respiration monitors, and ECG sensing electrodes, one or more environmental sensors such as atmospheric thermometers, airflow sensors, video sensors, audio sensors, accelerometers, GPS locators, and hygrometers. In these examples, the sensors may include sensors with a relatively low sampling rate, such as wireless sensors.

The components of the therapy delivery interface 116 couple one or more therapy delivery devices, such as capacitors, defibrillator electrode assemblies, pacing electrode assemblies, or mechanical chest compression devices, to the processor 118. It is appreciated that the functionality of the therapy delivery interface 116 may be incorporated into the sensor interface 114 to form a single interface coupled to the processor 118.

The components of the network interface 106 couple the processor 118 to a computer network via a networking device, such as a bridge, router or hub. According to a variety of examples, the network interface 106 supports a variety of standards and protocols, examples of which include USB (via, for example, a dongle to a computer), TCP/IP, Ethernet, Wireless Ethernet, Bluetooth®, ZigBee, M-Bus, CAN-bus, IP, IPV6, UDP, DTN, HTTP, FTP, SNMP, CDMA, NMEA and GSM. It is appreciated that the network interface 106 of external medical device controller 102 may enable communication between other medical device controllers within a certain range.

To ensure data transfer is secure, in some examples, the external medical device controller 102 can transmit data via the network interface 106 using a variety of security measures including, for example, TLS, SSL, or VPN. In some examples, the network interface 106 includes both a physical interface configured for wireless communication and a physical interface configured for wired communication. According to various examples, the network interface 106 enables communication between the external medical device controller 102 and a variety of personal electronic devices including, for example, computer enabled glasses, watches, and earpieces. In these examples, the network interface 106 may connect to and communicate through a body area network.

In one example, the network interface 106 is also capable of transmitting or receiving information to assist in medical device location determination. This may be accomplished through one or more antennas integrated with or coupled to the network interface 106, and consequently coupled to the processor 118. For example, the one or more antennas may receive GPS signals from satellites. The GPS signals may be used to determine the location of the medical device with a given level of accuracy or used to determine the current time.

Thus, the various system interfaces incorporated in the medical device controller 102 allow the device to interoperate with a wide variety of devices in various contexts. For instance, some examples of the medical device controller 102 are configured to perform a process of sending critical events and data to a centralized server via the network interface 106. An illustration of a process in accord with these examples is disclosed in U.S. Pat. No. 6,681,003, titled "DATA COLLECTION AND SYSTEM MANAGEMENT FOR SUBJECT-WORN MEDICAL DEVICES," issued on Jan. 20, 2004 which is hereby incorporated by reference in its entirety.

As illustrated in FIG. 1, the therapy delivery interface 116 and the network interface 106 are optional and may not be included in every example. For instance, a heart rate monitor may employ the medical device controller 102 to issue alarms but may not include a therapy delivery interface 116 to treat cardiac abnormalities. Similarly, an ambulatory defibrillator may include the medical device controller 102 to provide defibrillation functionality but may not include a network interface 106 where, for example, the ambulatory defibrillator is designed to rely on the user interface 108 to announce alarms.

Example User Interface Implementation

The user interface 108 shown in FIG. 1 includes a combination of hardware and software components that allow the medical device controller 102 to communicate with an external entity, such as a patient or other user. These components may be configured to receive information from actions such as physical movement, verbal intonation, or thought processes. In addition, the components of the user interface 108 can provide information to external entities. Examples of the components that may be employed within the user interface 108 include keyboards, mouse devices, trackballs, microphones, electrodes, touch screens, printing devices, display screens, and speakers. As discussed above, in one example, providing information to external entities includes displaying, communicating, or otherwise conveying a prompt to a patient. In one setting, this may include displaying sign language, such as American Sign Language (ASL), via the user interface 108. In some examples, the electrodes include an illuminating element, such as an LED. In some examples, the printing devices include printers capable of rendering visual or tactile (Braille) output. In one example, the user interface 108 incorporates a Braille mobile device, such as the LevelStar® Braille tablet commercially available from LevelStar LLC of Louisville, Colorado.

In some examples, the user interface 108 is configured to provide a custom prompt interface thorough which the medical device controller 102 receives custom prompt data. This custom prompt data may include: identifiers of previously defined prompts, definitions of new prompts, identifiers of previously defined target events that trigger prompts, definitions of new target events that trigger prompts, identifiers of previously defined responses to be addressed, definitions of new responses to be addressed, identifiers of previously defined actions to be taken in addressing responses, and definitions of new actions to be taken in addressing responses. In one example, information descriptive of target events may further include data descriptive of a target time period.

In one example, the custom prompt interface may be used by an authorized person, such as a health care professional treating a patient via an external medical device, to seek additional information from the patient via the external medical device. The additional information sought by the authorized person may include answers to direct, natural language questions, as may be presented in a health survey as discussed above. In some examples, the custom prompt interface may be used by an authorized person, such as a support technician, to provide natural language based instructions and training to a patient or a third party via the external medical device.

To initiate data collection or information distribution via the external medical device, the authorized person may access the custom prompt interface via the user interface 108. The custom prompt interface may employ a variety of metaphors and user interface elements. In one example, the custom prompt interface is rendered via the user interface 108 and exchanges information descriptive of instructions to alter custom prompt data stored on the external medical device. In response to receiving input requesting a change to the custom prompt data of the external medical device, the custom prompt interface processes the input and stores changes to the custom prompt data in a data store of the external medical device. Examples of user interface elements provided by the custom prompt interface are described further below with reference to FIGS. 7-9. Additional examples of processes executed by the custom prompt interface are described further below with reference to FIG. 10.

Other examples may include a variety of features not shown in FIG. 1. For instance, some examples may integrate an accelerometer/acoustic sensor and an electrode into a single assembly. In other examples, the accelerometer/acoustic sensor is integrated within a therapy electrode assembly. One such arrangement is described further in U.S. patent application Ser. No. 14/314,799, titled "THERAPEUTIC DEVICE INCLUDING ACOUSTIC SENSOR," filed Jun. 25, 2014, which is hereby incorporated herein by reference in its entirety. In other examples, the accelerometer/acoustic sensor is integrated within a garment such as the garment described further below with reference to FIG. 3. For instance, the accelerometer/acoustic sensor may be integrated within a belt, vest, or harness, such as the harness 310 or the belt 350. Thus the examples disclosed herein are not limited to a particular number or arrangement of accelerometer/acoustic sensors or electrodes.

Automated Speech Recognition (ASR)

In some implementations, the external medical device can include a voice recognition engine for detecting a voice of a user (e.g., patient, physician, PSR, or other human entity) and automatically adapting a corresponding output based on the recognition. For example, using automated speech recognition (ASR), a patient's verbal response to health survey questions can be recorded. In some examples, an original voice model can be adapted to individual dictators to improve an accuracy of the voice recognition engine. For example, in such applications, an ASR process can include an initial training/adaptation phase. In the training/adaptation phase, the engine can be adjusted to detect nuances in a speech spectrum based on different kinds of parameters, such as: the speaker's pitch, tone, etc., (e.g., certain speech features can be extracted using cepstral and spectral domain analysis), differentiation of male and female voices, languages, utterance speeds, accents, and/or dialects. In some examples, the training can also account for a type of microphone and processing engine used, and an ambience or environmental conditions, including, different kinds of noise inputs along with the speaker's audio.

In some examples, a process of adaptation to train the speaker's input for better ASR efficiency/accuracy can be performed online (e.g., based on incremental input) or offline (e.g., based on recorded audio batches as input). An online process can include an adaptation process that occurs as and when the speaker is providing inputs into the ASR engine for recognition. In this example, the engine can learn and adapt to the user's speech as more inputs and more words of the speaker's audio are being recognized. An offline process can include adaptation and/or training the ASR engine's models with a set of the speaker's audio corpora (typically as a batch audio) even before the user starts using the engine for recognition or transcription.

For example, in the context of a wearable ambulatory device, the offline adaptation can consist of a training/adaptation mode where the user is asked to speak some of the regularly used words by the speaker during the training. For instance, it may be known in advance that a patient may provide certain utterances in responding a health survey questions, such as "Yes," "No," or "May be," or in the context of describing physical feelings, "I am feeling fine," "I am feeling faint," "I feel tired," "My legs hurt." The patient may also be asked to speak certain words and/or phrases that can be used during a training or maintenance mode of the device. For example, the patient may state "I can hear the chime now," or "I cannot feel the vibration." Similarly, a physician specialized in a certain practice, such as cardiology, can be required to speak certain words and/or phrases that he or she is likely to use in customizing, e.g., a health survey. For example, the physician may also be required to speak certain medical terms such as "arrhythmia" or "cardiac arrest." In this manner, the ASR process can be trained for the specific contexts and environments of use.

In some implementations, another factor that can be used to improve an acoustic model may be based on supervised or unsupervised adaptation. In the case of supervised adaptation, there can be an existing baseline transcript based on how the acoustic models are trained. In unsupervised adaptation, there may be no transcript and usually the more new words are spoken, the better the adaptation for the acoustic models. In unsupervised adaptation, spoken words can be aligned with a baseline model and use the transcribed words for adaptation. Those skilled in the art will understand that, in some examples, a confidence measure can be used to learn whether certain transcribed words may be used for adaptation or not. For example, Hidden Markov Model-based recognition engines may use an unsupervised or a mixture of supervised/unsupervised schemes to perform adaptation.

In some examples, an audio input of a predetermined length may be used to perform the training. For example, the audio duration may comprise in a range of 1-30 minutes of audio input. Persons of ordinary skill can understand that additional processes may be performed on the ASR process to improve quality, including compression, filtering, or other signal processing algorithms.

Figure 2B:
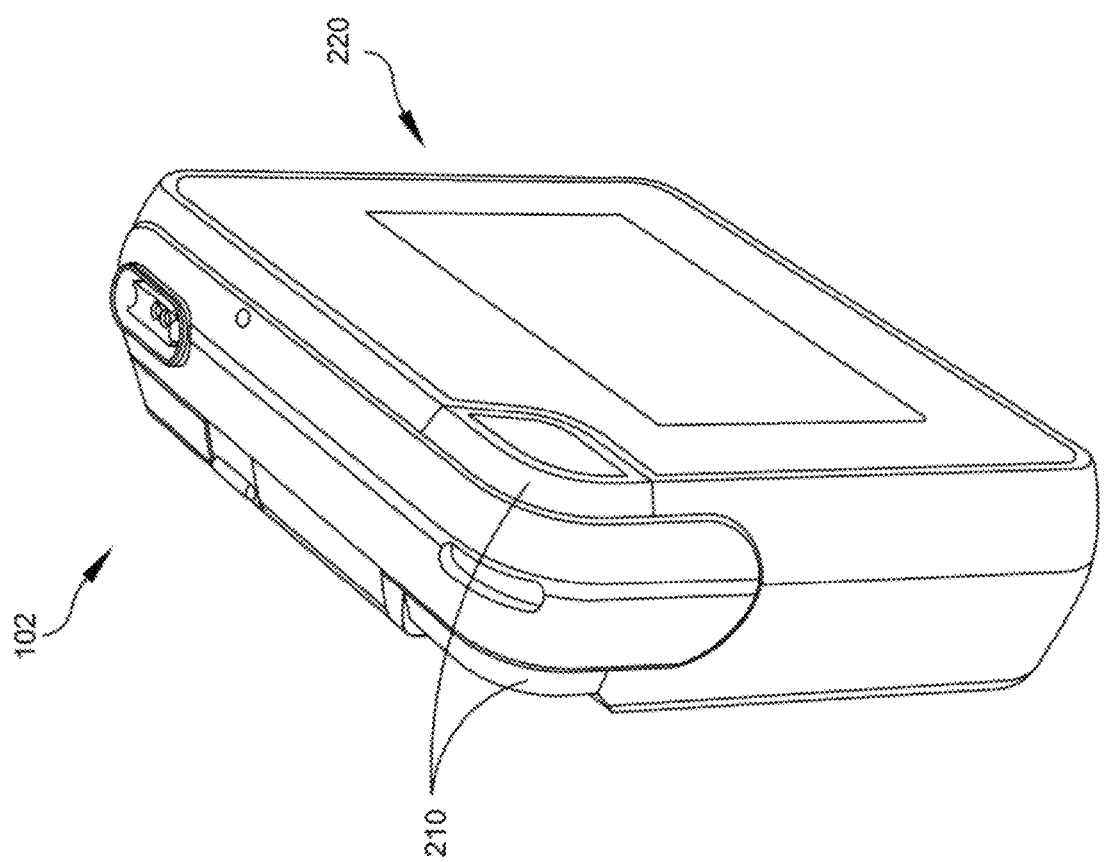
FIGS. 2A-B are illustrations of one example of an external medical device controller for an external medical device.
Figure 2A:
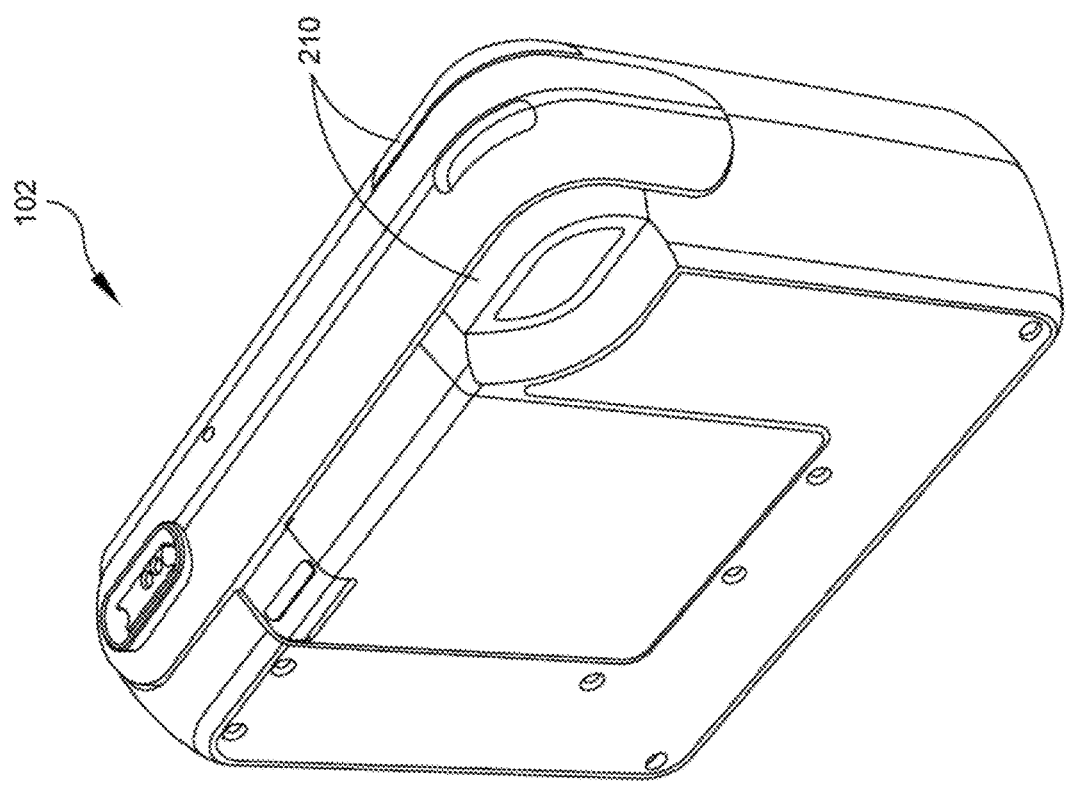

In some examples, the medical device controller 102 is incorporated into a unitary housing. FIGS. 2A-B illustrate such an example of the medical device controller 102. As shown in FIGS. 2A-B, the medical device controller 102 includes two response buttons 210 on opposing sides of the housing. The response buttons 210 are recessed to reduce the likelihood of accidental activation (e.g., a patient falling on the response button). The medical device controller 102 also includes, in this example, a display screen 220 and a speaker to enable the communication of audible and visual stimuli to the patient. It is appreciated that the response buttons 210 do not have to be placed on opposing sides of the housing as illustrated in FIGS. 2A-B. The response buttons, for example, may be located adjacent to each other in the housing the medical device controller 102. The adjacent placement of the response buttons may make it easier for individuals with smaller hands or less dexterity to engage the response buttons.

Example Ambulatory Medical Device

Figure 3:
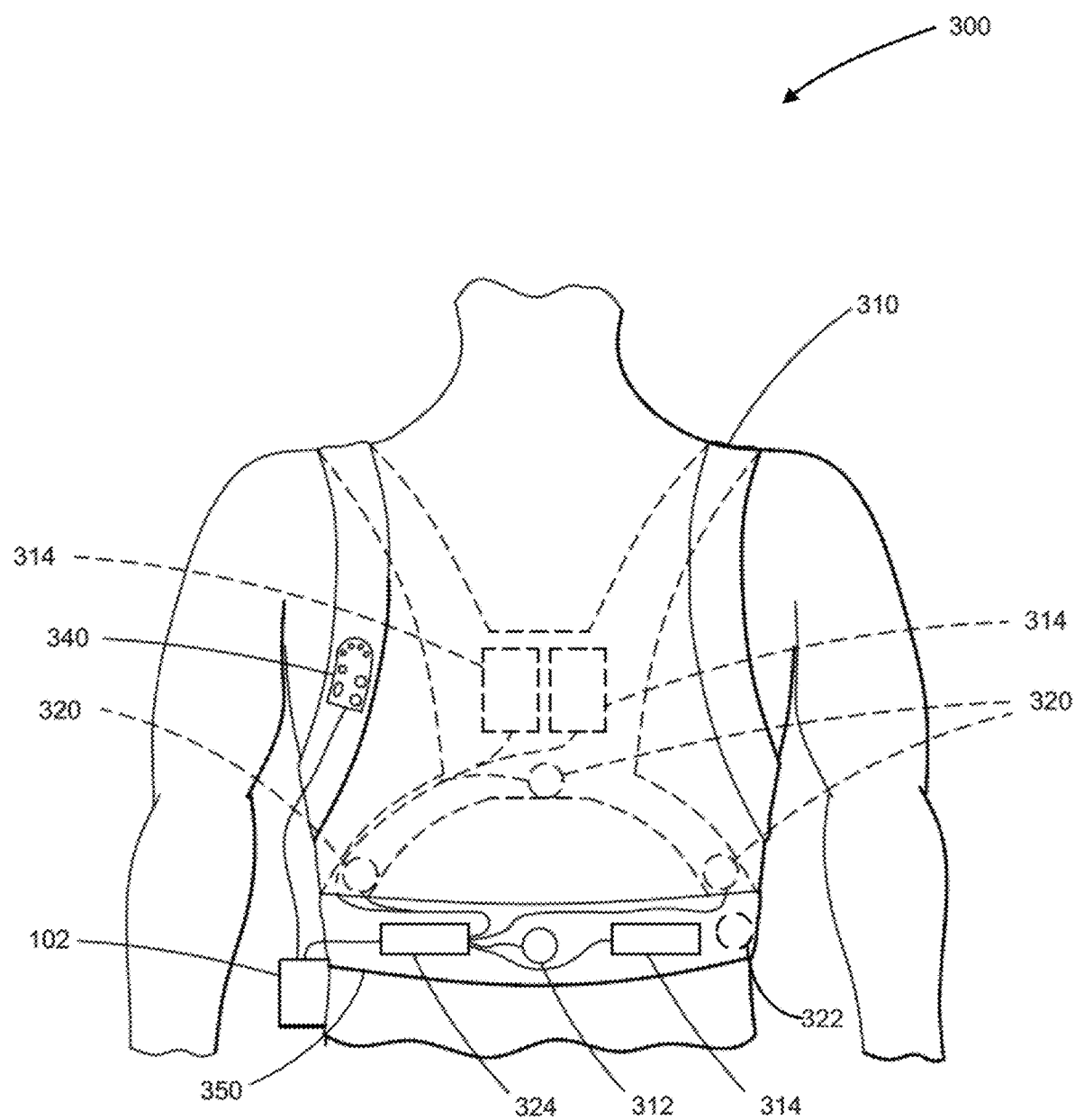
FIG. 3 is an illustration of one example of an external medical device.

In some examples, the external medical device controller 102 described above with reference to FIG. 1 is included in a wearable defibrillator comprising a garment (e.g., a vest or belt) that is worn by the patient. FIG. 3 illustrates a wearable defibrillator 300 in accord with these examples. In at least one example, the wearable defibrillator 300 may be a LifeVest® wearable cardioverter defibrillator available from ZOLL Medical Corporation of Chelmsford, Massachusetts. The wearable defibrillator 300 monitors the patient's ECG with sensing electrodes, monitors the patient heart sounds with acoustic sensors, detects life-threatening arrhythmias, records events of interest, and delivers therapy in the form of one or more pacing pulses or a defibrillating shock through the therapy electrodes if treatment is necessary. As shown in FIG. 3, the wearable defibrillator 300 includes a harness 310 having a pair of shoulder straps and a belt that is worn about the torso of a patient. The wearable defibrillator 300 includes a plurality of ECG sensing electrodes 320 that are attached to the harness 310 at various positions about the patient's body and electrically coupled to the sensor interface 114 of the medical device controller 102 via a connection pod 324. The plurality of ECG sensing electrodes 320 are coupled to the medical device controller 102 to monitor the cardiac function of the patient and generally include an anterior/posterior pair of ECG sensing electrodes and a side/side pair of ECG sensing electrodes. The plurality of ECG sensing electrodes 320 may incorporate any electrode system, including conventional stick-on adhesive electrodes, dry-sensing capacitive ECG electrodes, radio transparent electrodes, segmented electrodes, or one or more long term wear electrodes that are configured to be continuously worn by a patient for extended periods (e.g., 3 or more days). One example of such a long term wear electrode is described in U.S. Patent Application Publication No. 2013/0325096, titled "LONG TERM WEAR MULTIFUNCTION BIOMEDICAL ELECTRODE," published Dec. 5, 2013, which is hereby incorporated herein by reference in its entirety. Additional ECG sensing electrodes may be provided, and the plurality of ECG sensing electrodes 320 may be disposed at various locations about the patient's body.

The wearable defibrillator 300 also includes one or more accelerometer/acoustic sensors 322 that are attached to a belt 350 of the harness 310 at various positions about the patient's body and electrically coupled to the sensor interface 114 of the medical device controller 102 via the connection pod 324. The one or more accelerometer/acoustic sensors 322 are coupled to the medical device controller 102 to monitor the cardiopulmonary function of the patient and generally positioned on the surface of a patient's body in the precordial area.

Although not shown is FIG. 3, the wearable defibrillator 300 may include additional sensors, other than the plurality of ECG sensing electrodes 320, capable of monitoring the physiological condition or activity of the patient. For example, sensors capable of measuring blood pressure (via, for example, video blood pressure detection), heart rate, heart sounds, thoracic impedance, pulse oxygen level (via, for example, reflectance-based pulse oximetry to determine oxygen concentration), respiration rate, and the activity level of the patient may also be provided.

The wearable defibrillator 300 also includes a plurality of therapy electrodes 314 that are electrically coupled to the medical device controller 102 via the connection pod 324 and which are configured to deliver one or more therapeutic defibrillating shocks to the body of the patient, if it is determined that such treatment is warranted. Each therapy electrode of the plurality of therapy electrodes may be housed in a therapy electrode assembly that further includes conductive gel disposed within one or more reservoirs. Prior to delivering therapy, the therapy electrode assembly may dispense the conductive gel to improve conductivity between the therapy electrode and the body of the patient. The connection pod 324 electrically couples the plurality of ECG sensing electrodes 320 and the plurality of therapy electrodes 314 to the therapy delivery interface 116 of the medical device controller 102, and may include electronic circuitry configured for this purpose. The connection pod 324 may also include other electronic circuitry, such as a motion sensor or accelerometer through which patient activity may be monitored.

As shown in FIG. 3, the wearable defibrillator 300 also includes a user interface pod 340 that is electrically coupled to, or integrated in with, the user interface 108 of the medical device controller 102. The user interface pod 340 can be attached to the patient's clothing or to the harness 310, for example, via a clip (not shown) that is attached to a portion of the interface pod 340. In some examples, the user interface pod 340 may simply be held in a person's hand. In some examples, the user interface pod 340 may communicate wirelessly with the user interface 108 of the medical device controller 102, for example, using a Bluetooth®, Wireless USB, ZigBee, Wireless Ethernet, GSM, or other type of communication interface.

Example Automated Medical Device

Figure 4:
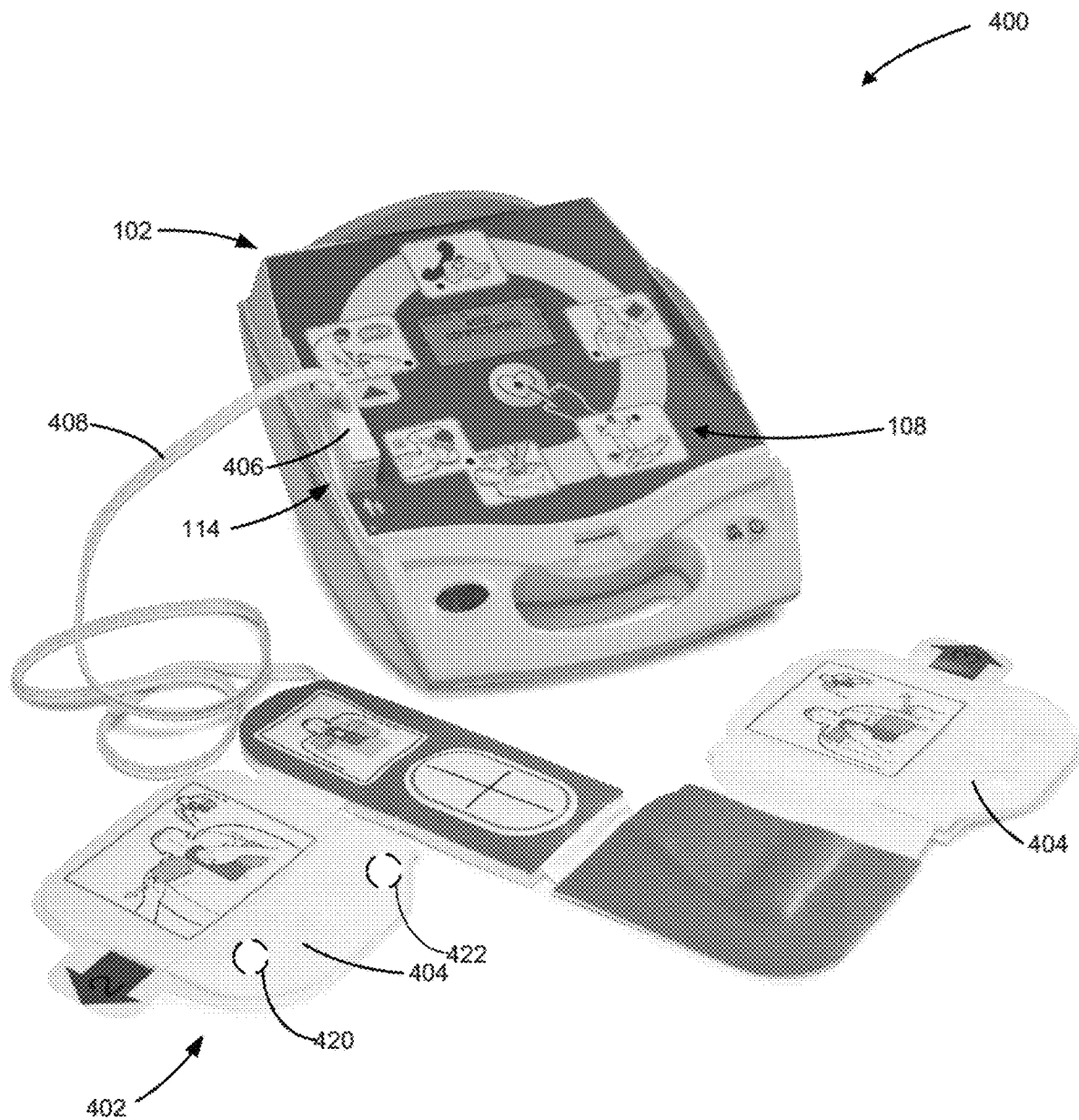
FIG. 4 is an illustration of one example of an external medical device.

In some examples, the external medical device controller 102 described above with reference to FIG. 1 is included in an automated external medical device (AED). AEDs are small portable defibrillators that are capable of monitoring cardiac rhythms, determining when a defibrillating shock is necessary, and administering the defibrillating shock either automatically, or under the control of a trained rescuer (e.g., an EMT or other medically trained personnel). The AED, in addition, may be configured to provide counseling to an operator as to how to perform cardiac resuscitation (CPR). FIG. 4 illustrates an AED 400. The AED 400 may be, for example, an AED Plus® automated external defibrillator available from ZOLL Medical Corporation of Chelmsford, Massachusetts. As shown, the AED 400 includes the medical device controller 102 and an electrode assembly 402.

The electrode assembly 402 includes one or more sensing electrodes (e.g., ECG sensors), one or more acoustic sensors 422, one or more therapy electrodes 404 (e.g., defibrillation pads), a connector 406, wiring 408 electrically coupling the connector 406 to the one or more sensing electrodes 420, the one or more acoustic sensors, and the one or more therapy electrodes 404. As shown in FIG. 4, the connector is configured to couple the electrode assembly 402 to the medical device controller 102 and, more specifically, the one or more sensing electrodes 420 and the one or more acoustic sensors 422 to the sensor interface 114 and the one or more therapy electrodes to the therapy delivery interface 116.

The medical device controller 102 of the AED 400 is configured to detect the cardiac rhythm of the patient using ECG and heart sounds data and provide pacing and defibrillating shocks to the patient as appropriate. This process is similar to the process described with regard to medical device controller 102 of the ambulatory medical device 300. The user interface 108 of the AED 400 may include a variety of components configured to communicate with the operator including, but not limited to, a display screen, a speaker, and one or more buttons. In this example, the AED 400 includes a display screen to display notifications to an operator. The notifications may provide instructions to the operator regarding the proper administration of CPR to the patient. The notifications on the display may be accompanied by audible alarms from the speaker to further assist the operator in administering CPR to the patient.

In another example, the medical device controller 102 (and more particularly, the natural language processing component of FIG. 1) of the AED is configured to use processed acoustic data to guide an operator through a CPR procedure. In this example, the natural language processing component 112 issues step by step instructions to the operator and analyzes processed electrode data, processed acoustic data, and processed motion data representative of heart sounds, breath sounds, and physical movement (e.g., chest compressions) to validate performance of each step by the operator. Further, where performance of a given step is inadequate (e.g., chest compressions are not deep enough), the natural language processing component 112 may issue additional instructions to help the operator adequately perform the given step.

Example Prompting Computer System

Figure 5:
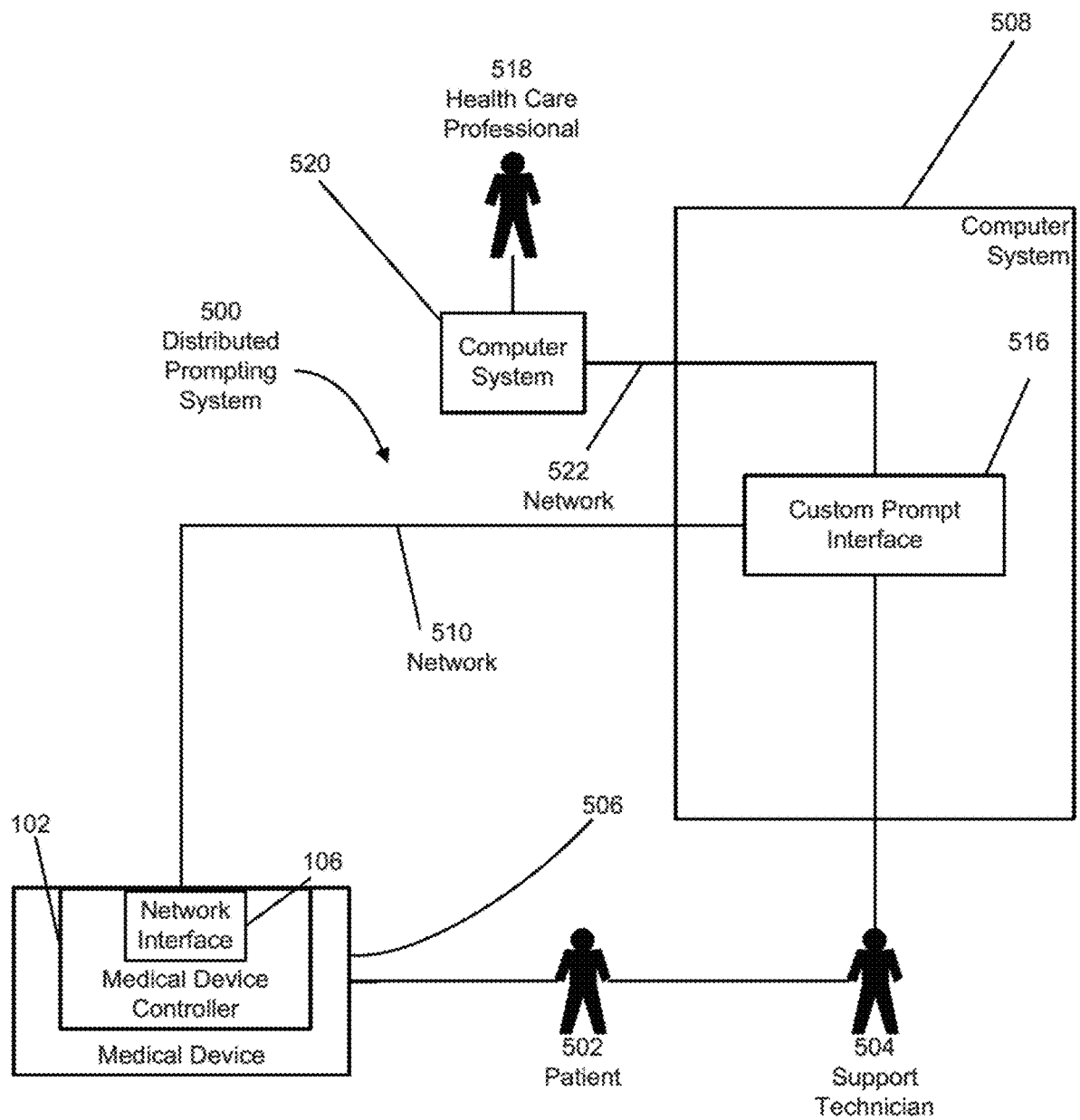
FIG. 5 is a block diagram of one example of a distributed prompting system.

As discussed above, some examples provide health survey prompts, training prompts, and instruction prompts to a user that are tailored to the needs of the user, the user's language, and the user's situation. FIG. 5 illustrates one of these examples, a distributed prompting system 500. As shown, FIG. 5 includes a patient 502, a support technician 504, a health care professional 518, the external medical device 506, computer systems 508 and 520, and communication networks 510 and 522. The computer system 508 includes a custom prompt interface 516. While shown in FIG. 5 as included in the distributed prompting system 500, in various examples the custom prompt interface is incorporated into the external medical device 506 and does not require a network connection. The external medical device 506 may include any programmable device (a device including memory for storing data and at least one processor in data communication with the memory) configured to monitor and potentially treat patients, such as the external medical devices described above with reference to FIGS. 3 and 4. As shown in FIG. 5, the medical device 506 includes the medical device controller 102. The medical device controller 102 includes the network interface 106. Both the medical device controller and the network interface 106 are described above with reference to FIG. 1. The computer system 508 may include one or more computer systems, such as the computer system described below with reference to FIG. 6. In particular, the computer system may include mobile computing devices (e.g., smart phones, tablet computers, personal digital assistants, etc.).

As depicted in FIG. 5, the computer system 508 and the external medical device 506 exchange (i.e. send or receive) information via the network 510. Similarly, the computer system 520 and the computer system 508 exchange information via the network 522. The network 510 or the network 522 may include any communication network through which programmable devices may exchange information. For example, the network 510 or the network 522 may be a public network, such as the internet, and may include other public or private networks such as LANs, WANs, extranets, intranets, and cloud computing systems. The network 510 or the network 522 may also include cellular networks such as CMDA, EvDO, GSM, and iDEN networks. Although the network 510 and the network 522 are illustrated as distinct networks in FIG. 5, examples disclosed herein are not limited to two distinct networks. The network 510 and the network 522 may be a unified, connected network or may include other networks without departing from the scope of the examples disclosed herein.

In some examples, an authorized person, such as a health care professional 518 treating the patient 502 via the external medical device 506, seeks additional information from the patient 502 via the external medical device 506. The additional information sought by the authorized person may include answers to direct questions, as may be presented in a health survey as discussed above.

To initiate information collection via the external medical device 506, the health care professional 518 may instruct the support technician 504 to alter prompt information of the external medical device by conducting an update process. In some examples, the health care professional 518 may communicate these instructions via the custom prompt interface 516. In these examples, the custom prompt interface 516 includes a secure, web based, storage and retrieval system for information gathered by external medical devices, such as the external medical device 506. Using the custom prompt interface 516, health care professionals (e.g., the health care professional 518) can access data for patients (e.g. the patient 502) wearing devices (e.g., the external medical device 506) and monitor the patient's medical condition, review responses to prompts, review alert histories, and the like.

In one example illustrated in FIG. 5, the custom prompt interface 516 serves a secure user interface to the health care professional 518 via the network 522 and the computer system 520. The computer system 520 renders the user interface and exchanges information descriptive of instructions to alter the configuration of the external medical device 506 with the health care professional 518. In response to receiving input requesting a change to the configuration of the external medical device, the custom prompt interface 516 processes the information and provides the instructions to the support technician 504. To exchange information with the health care professional 518, the custom prompt interface 516 may employ a variety of metaphors and user interface elements. Examples of user interface elements served by the custom prompt interface 516 and rendered by the computer system 520 are described further below with reference to FIGS. 7-9.

In some examples, and as illustrated in FIG. 5, the computer system 508 also renders the custom prompt interface 516 to the support technician 504. When rendered to the support technician 504, the custom prompt interface 516 is configured to exchange information with the support technician 504 and the external medical device 506. The information processed by the custom prompt interface 516 may include requests to change prompt information, requests for authorization, requests for update sessions, requests for authentication, requests to initiate updates, requests to process acknowledgments, and the like. To exchange information with the external medical device 506, the custom prompt interface 516 generates and transmits messages to the external medical device 506 that subscribe to a protocol supported by the external medical device 506. To exchange information with the support technician 504, the custom prompt interface 516 may employ a variety of metaphors and user interface elements. For instance, in one example, the custom prompt interface 516 includes a support interface with screens and other elements that, when selected by the support technician 504, prompt the support technician 504 to enter a request to change parameters of the external medical device 506. Further, in this example, the support interface includes elements configured to initiate transmission of altered configuration information, including custom prompt data, from the computer system 508 to the external medical device 506. Responsive to receiving the altered configuration information, the external medical device processes the altered configuration information and adjusts its operation accordingly. Additional examples of processes and acts that the distributed prompting system is configured to execute are described below with reference to FIG. 10.

Computer System

As discussed above with regard to FIG. 5, various aspects and functions described herein may be implemented as specialized hardware or software components executing in one or more computer systems. There are many examples of computer systems that are currently in use. These examples include, among others, network appliances, personal computers, workstations, mainframes, networked clients, servers, media servers, application servers, database servers, and web servers. Other examples of computer systems may include mobile computing devices (e.g., smart phones, tablet computers, laptop computers, and personal digital assistants) and network equipment (e.g., load balancers, routers, and switches). Examples of particular models of mobile computing devices include iPhones, iPads, and iPod touches running iOS operating system available from Apple, Android devices like Samsung Galaxy Series, LG Nexus, and Motorola Droid X, Blackberry devices available from Blackberry Limited, and Areas Phone devices. Further, aspects may be located on a single computer system or may be distributed among a plurality of computer systems connected to one or more communications networks.

For example, various aspects, functions, and processes may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Consequently, examples are not limited to executing on any particular system or group of systems. Further, aspects, functions, and processes may be implemented in software, hardware or firmware, or any combination thereof. Thus, aspects, functions, and processes may be implemented within methods, acts, systems, system elements and components using a variety of hardware and software configurations, and examples are not limited to any particular distributed architecture, network, or communication protocol.

Figure 6:
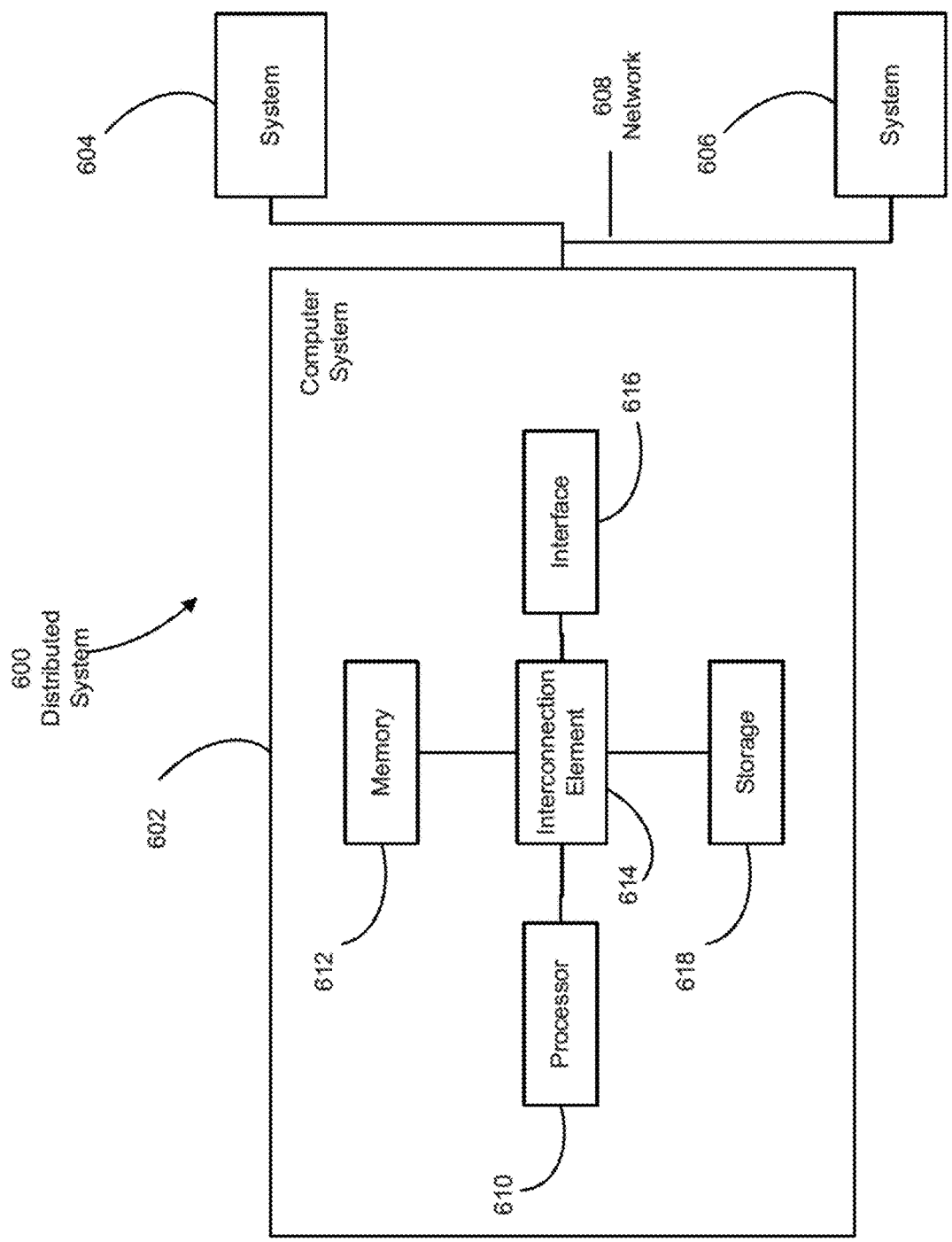
FIG. 6 is a block diagram of one example of a distributed computing system.

Referring to FIG. 6, there is illustrated a block diagram of a distributed computer system 600, in which various aspects and functions are practiced. As described above with reference to FIG. 5, in at least one example, the computer system 508 includes one or more distributed computer systems such as the computer system 600. As shown in FIG. 6, the distributed computer system 600 includes one more computer systems that exchange information. More specifically, the distributed computer system 600 includes computer systems 602, 604, and 606. As shown, the computer systems 602, 604, and 606 are interconnected by, and may exchange data through, a communication network 608. The network 608 may include any communication network through which computer systems may exchange data. To exchange data using the network 608, the computer systems 602, 604, and 606 and the network 608 may use various methods, protocols and standards, including, among others, Fibre Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST, and Web Services. To ensure data transfer is secure, the computer systems 602, 604, and 606 may transmit data via the network 608 using a variety of security measures including, for example, TLS, SSL, or VPN. While the distributed computer system 600 illustrates three networked computer systems, the distributed computer system 600 is not so limited and may include any number of computer systems and computing devices, networked using any medium and communication protocol.

As illustrated in FIG. 6, the computer system 602 includes a processor 610, a memory 612, an interconnection element 614, an interface 616 and data storage element 618. To implement at least some of the aspects, functions, and processes disclosed herein, the processor 610 performs a series of instructions that result in manipulated data. The processor 610 may be any type of processor, multiprocessor or controller. Some exemplary processors include commercially available processors such as an Intel Xeon, Itanium, Core, Celeron, or Pentium processor, an AMD Opteron processor, an Apple A4 or A5 processor, a Sun UltraSPARC or IBM Power5+ processor and an IBM mainframe chip. The processor 610 is connected to other system components, including one or more memory devices 612, by the interconnection element 614.

The memory 612 stores programs and data during operation of the computer system 602. Thus, the memory 612 may be a relatively high performance, volatile, random access memory such as a dynamic random access memory ("DRAM") or static memory ("SRAM"). However, the memory 612 may include any device for storing data, such as a disk drive or other nonvolatile storage device. Various examples may organize the memory 612 into particularized and, in some cases, unique structures to perform the functions disclosed herein. These data structures may be sized and organized to store values for particular data and types of data.

Components of the computer system 602 are coupled by an interconnection element such as the interconnection element 614. The interconnection element 614 may include any communication coupling between system components such as one or more physical busses in conformance with specialized or standard computing bus technologies such as IDE, SCSI, PCI and InfiniBand. The interconnection element 614 enables communications, such as data and instructions, to be exchanged between system components of the computer system 602.

The computer system 602 also includes one or more interface devices 616 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 602 to exchange information and to communicate with external entities, such as users and other systems.

The data storage element 618 includes a computer readable and writeable nonvolatile, or non-transitory, data storage medium in which instructions are stored that define a program or other object that is executed by the processor 610. The data storage element 618 also may include information that is recorded, on or in, the medium, and that is processed by the processor 610 during execution of the program. More specifically, the information may be stored in one or more data structures specifically configured to conserve storage space or increase data exchange performance. The instructions may be persistently stored as encoded signals, and the instructions may cause the processor 610 to perform any of the functions described herein. The medium may, for example, be optical disk, magnetic disk or flash memory, among others. In operation, the processor 610 or some other controller causes data to be read from the nonvolatile recording medium into another memory, such as the memory 612, that allows for faster access to the information by the processor 610 than does the storage medium included in the data storage element 618. The memory may be located in the data storage element 618 or in the memory 612, however, the processor 610 manipulates the data within the memory, and then copies the data to the storage medium associated with the data storage element 618 after processing is completed. A variety of components may manage data movement between the storage medium and other memory elements and examples are not limited to particular data management components. Further, examples are not limited to a particular memory system or data storage system.

Although the computer system 602 is shown by way of example as one type of computer system upon which various aspects and functions may be practiced, aspects and functions are not limited to being implemented on the computer system 602 as shown in FIG. 6. Various aspects and functions may be practiced on one or more computers having a different architectures or components than that shown in FIG. 6. For instance, the computer system 602 may include specially programmed, special-purpose hardware, such as an application-specific integrated circuit ("ASIC") tailored to perform a particular operation disclosed herein. Another example may perform the same function using a grid of several general-purpose computing devices running MAC OS System X with Motorola PowerPC processors and several specialized computing devices running proprietary hardware and operating systems.

The computer system 602 may be a computer system including an operating system that manages at least a portion of the hardware elements included in the computer system 602. In some examples, a processor or controller, such as the processor 610, executes an operating system. Examples of a particular operating system that may be executed include a Windows-based operating system, such as, Windows NT, Windows 2000 (Windows ME), Windows XP, Windows Vista or Windows 7 operating systems, available from the Microsoft Corporation, a MAC OS System X operating system or an iOS operating system available from Apple Computer, one of many Linux-based operating system distributions, for example, the Enterprise Linux operating system available from Red Hat Inc., a Solaris operating system available from Sun Microsystems, or a UNIX operating systems available from various sources. Many other operating systems may be used, and examples are not limited to any particular operating system.

The processor 610 and operating system together define a computer platform for which application programs in high-level programming languages are written. These component applications may be executable, intermediate, bytecode or interpreted code which communicates over a communication network, for example, the Internet, using a communication protocol, for example, TCP/IP. Similarly, aspects may be implemented using an object-oriented programming language, such as .Net, SmallTalk, Java, C++, Ada, C# (C-Sharp), Python, or JavaScript. Other object-oriented programming languages may also be used. Alternatively, functional, scripting, or logical programming languages may be used.

Additionally, various aspects and functions may be implemented in a non-programmed environment. For example, documents created in HTML, XML or other formats, when viewed in a window of a browser program, can render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Accordingly, the functional components disclosed herein may include a wide variety of elements (e.g., specialized hardware, executable code, data structures or objects) that are configured to perform the functions described herein.

In some examples, the components disclosed herein may read parameters that affect the functions performed by the components. These parameters may be physically stored in any form of suitable memory including volatile memory (such as RAM) or nonvolatile memory (such as a magnetic hard drive). In addition, the parameters may be logically stored in a propriety data structure (such as a database or file defined by a user mode application) or in a commonly shared data structure (such as an application registry that is defined by an operating system). In addition, some examples provide for both system and user interfaces that allow external entities to modify the parameters and thereby configure the behavior of the components.

Example Prompting Interfaces

FIG. 7 shows one example interface configured to receive input selecting one or more customized prompts for transmission to an external medical device, such as those discussed above with reference to FIGS. 3 and 4. As shown, the interface 700 includes one or more user interface screens having a plurality of tabs 702 each having an associated topic, such as "Alerts", "Wear Time", "All Recordings", "Trends", "Trend Setup", "Setup Info", "Health Survey Setup", and "Walk Test Setup". In further examples, the interface 700 may include tabs not shown in FIG. 7. User interface elements associated with each individual tab 702 of the interface 700 are presented to the user responsive to user selection of the individual tab. FIG. 7 shows user selection of the "Health Survey Setup" tab 704.

According to one example, the "Health Survey Setup" tab 704 provides check boxes, text boxes, scroll boxes, or any other input components configured to receive selections of user defined customized prompts. As shown in FIG. 7, users may define health survey prompts including one or more questions. In one example, the "Health Survey Setup" tab 704 includes a listing of prompts 706 to communicate to a patient using natural language (e.g., audio prompts). Various prompts 706 may be, e.g., predefined and displayed in a listing, each having an associated check box 708 selectable by the user. Responsive to user selection of an associated check box 708, the interface 700 may display a confirmation symbol (e.g., check mark) proximate the check box 708 of the prompt 706 selected. User selection of individual prompts 706 permits the user of the interface 700 to customize a prompt-based health survey to be communicated to an associated patient. Tab 704 is shown as including at least the following prompts 706: "How many pillows did you sleep on last night?"; "Has your weight changed from yesterday?"; "How much activity have you averaged in the past few days?"; "Have you felt dizzy"; "Are you feeling fatigued"; "Are you having difficulty climbing the stairs?"; "Have you felt your heart racing"; "Have you felt your heart beating irregularly?"; "Are you short of breath?"; "Do you have swelling in your ankles and legs?"; "Have you had any chest pain?"; and "Have you missed any medications", but the examples disclosed herein are not be limited to these prompts 706.

In various examples, the interface 700 may include one or more text boxes configured to add a new prompt to the listing responsive to receiving an input of the new custom prompt in the text box. Accordingly, a user of the system may customize the listing of prompts 706 shown in the "Health Survey Setup" tab 704. In some examples, users can be granted different access-levels to modify the prompt data. Such user access-levels can result in certain rights being granted to users of the interface 700. For example, access-level rights can be managed using default or specified access control features provided in an operating system of the medical device controller. For example, a physician may be granted rights to edit the content of the custom prompts 706 and/or specify new prompts. A nurse, on the other hand, may be restricted to only selecting one or more predefined prompts 706 that were, e.g., previously set by the physician.

According to one example, the "Health Survey Setup" tab 704 includes a disable feature switch 710, a daily switch 712, and a weekly switch 714. Responsive to user selection of the disable switch 710, the daily switch 712, or the weekly switch 714, one or more components of an external medical device, such as the controller 102 discussed above with regards to FIG. 1, are configured to communicate, or refrain from, communicating the user selected prompts 706 via the external medical device. User selection of the disable switch 710 configures the external medical device to not communicate a health survey, user selection of the daily switch 712 configures the external medical device to issue the selected prompts on a daily schedule, and user selection of the weekly switch configures the external medical device to issue the selected prompts on a weekly schedule. While not shown, in further examples the interface may include a scheduling calendar, or one or more text boxes configured to receive dates or times at which to communicate the user selected prompts. In still further examples, the interface 700 may permit the user to select periods of delay for which the refrain from communicating. For example, a user may select via the interface 700 to refrain from communicating the prompts 706 during the nighttime hours of 1 AM to 5 AM. As discussed further below with reference to FIG. 10, the interface 700 may store the scheduling information discussed above within custom prompt data as one or more target events (e.g., prompt times) associated with the prompts.

According to one example, the "Health Survey Setup" tab 704 includes a number of iterations display 716 including an indefinitely switch 718 and an enter number switch 720. The enter number switch 720 may have an associated enter number text box 722. Responsive to user selection of the indefinitely switch 718 or the enter number switch 720, one or more components of an external medical device, such as the controller 102 discussed above with regards to FIG. 1, are configured to communicate the user selected custom prompts 706 via an associated external medical device for a number of iterations. User selection of the indefinitely switch 718 configures the external medical device to communicate the user selected prompts 706 in perpetuity (i.e., until the external medical device is reconfigured or placed out of service), whereas user selection of the enter number switch 720 configures the external medical device to communicate the selected prompts 706 the number of times identified by the user in the enter number text box 722. Accordingly, the user of the interface 700 may predetermine the volume of communications sent to the external medical device.

In one example, the "Health Survey Setup" tab 704 further includes a save indicator 724 configured to store user selections and preferences responsive to activation of the save indicator 724. For example, user selections may be stored in profiles accessible through a drop-down menu, such as menu 726. As shown in FIG. 7, responsive to user selection of the drop down menu 726, the interface 700 may present the user with one or more profiles of stored user selections. Profiles may be presented via a single selectable identifier, such as a date, name, user, health condition, health care provider, etc. Responsive to selection of the identifier, the interface 700 pre-populates the user selectable options (e.g., prompts 706, disable feature switch 710, daily switch 712, weekly switch 714, etc.) in the "Health Survey Setup" tab 704. Accordingly, users of the interface 700 may save and return to prompt 706 selections at any time. Alternatively, the interface 700 may include a List Manager indicator 728. Responsive to selection of the List Manager indicator 728, the interface 700 may display a comprehensive listing of all the stored profiles of stored user selections.

Turning now to FIG. 8, shown is a "Health Survey Results Review" tab 802. As discussed herein, one or more examples store data descriptive of one or more prompts to be provided to a user to initiate a response from the user. According to one example, the "Health Survey Setup" tab 704 provides check boxes, text boxes, scroll boxes, lists, areas, and any other display permitting a user to view and interact with customized prompts and associated responses.

In one example, the "Health Survey Results Review" tab 802 includes a listing of prompts 804. In various examples, the listing of prompts 804 may be included in a survey. As discussed above with reference to FIG. 7, prompts 804 may include customized health survey prompts including one or more questions. In various examples, the listing of prompts 804 includes the prompts 706 selected by the user in Health Survey Review tab 702. The "Health Survey Results Review" tab 802 may additionally present a listing of responses 806. In various examples, each response 806 corresponds to a prompt 804 in the listing of prompts. For example, each response 806 may include an answer to the question posed by the associated prompt 804. For purpose of illustration, the response to the prompt "How many pillows did you sleep on last night?" is "1". Responses 806 may include a description of an answer received from a patient of an external medical device. In various examples, this may include, numbers, colors, descriptive words, phrases, times, addresses, sentences, noises, sounds, yes/no answers, and etc. While not shown in FIG. 8, the "Health Survey Results Review" tab 802 may further include one or more navigational tools permitting the user to navigate through the listing of prompts 804 or responses 806.

In one example, the Health Survey Results Review tab 802 further includes a date performed scroll box 808, including a listing of the dates and times at which prompts 804 were communicated, or responses 806 were received. As shown in FIG. 8, the date performed scroll box 808 may display each listing of prompts 804 and responses 806 having a particular date or time via a date identifier 810. Responsive to selection of the date identifier 810, the "Health Survey Results Review" tab 802 is configured to display the listing of prompts 804 and responses 806 associated with that selected time period. Accordingly, the date performed scroll box 808 permits the user to navigate between listings of prompts 804 and associated listings of responses 806.

In one example, the "Health Survey Results Review" tab 802 further includes an additional health surveys 812 feature. In one example this may include a previous indicator 814. Responsive to user selection of the previous indicator 814, the "Health Survey Results Review" tab 802 presents a previously performed listing of prompts and responses. As discussed above, this listing may include a previously performed survey. For example, the previously performed survey may include repeated prompts at an earlier date, or prompts and responses for a common patient. Accordingly, the Health Survey Results Review tab 802 may also display an indicator 816 of the amount of surveys performed for a particular patient.

In one example, the "Health Survey Results Review" tab 802 may further include a trend indicator 818. Responsive to user selection of the trend indicator, the interface 700 may cause trends in patient responses and other trends related data to be displayed (e.g., user interface elements associated with the "Trends" tab shown in FIGS. 7-8).

Figure 9:
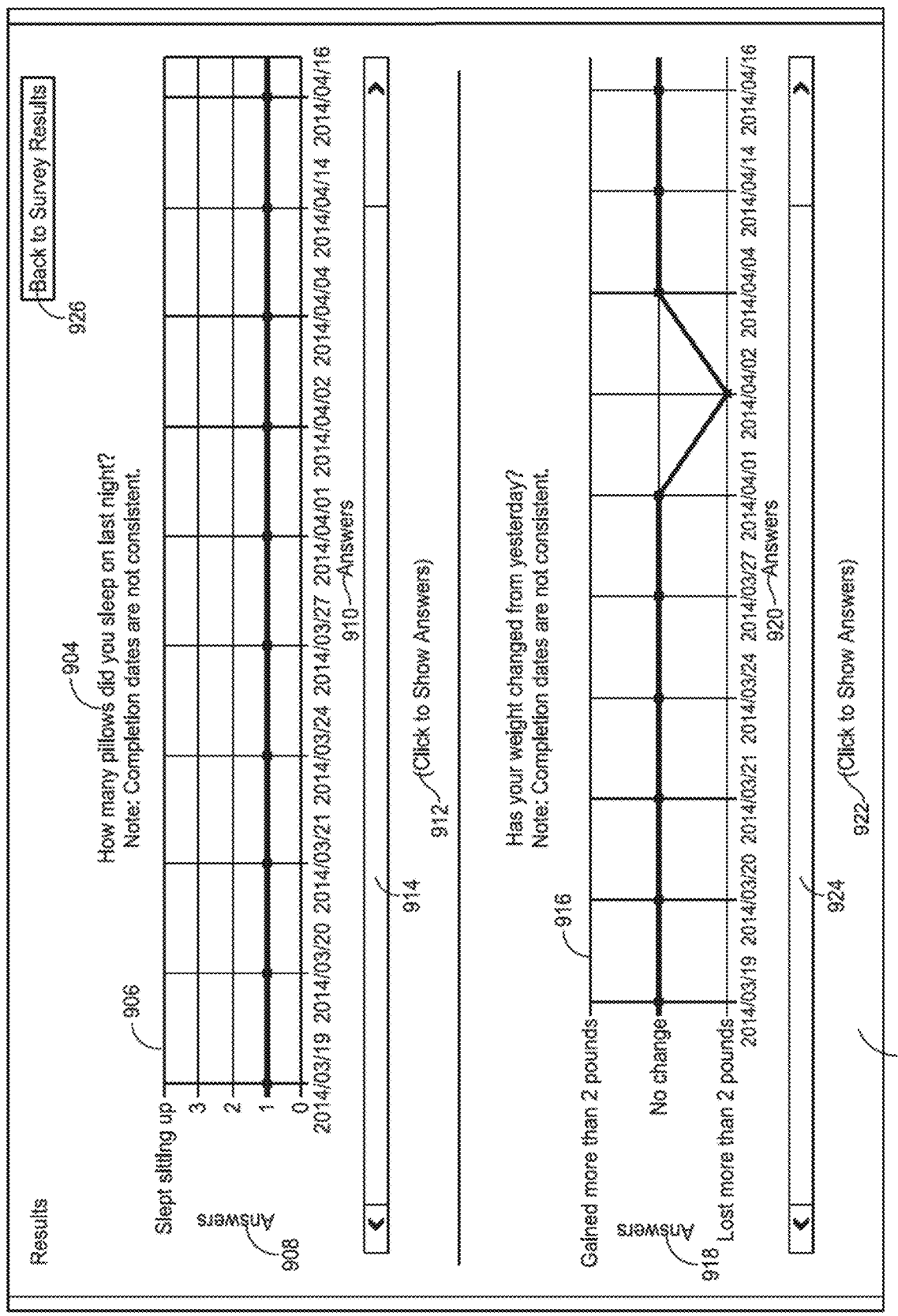
FIG. 9 is an illustration of one example of health survey results screen.

Turning now to FIG. 9, shown is a "Trend" tab 902. In various examples, the "Trend" tab 902 presents one or more visual representations of responses, such as the responses 806 of FIG. 8, for a particular prompt 904, such as prompts 706 or prompts 804, over a period of time. In various examples, the "Trend" tab 902 includes a visual representation for each prompt included in a listing of prompts, such as a survey. As shown in FIG. 9, visual representations may include graphs, charts, figures, and images, among other graphic representations. In particular, FIG. 9 shows a first visual representation 906 of responses to the prompt "How many pillows did you sleep on last night?" Responses for this prompt are indicated along the vertical axis 908 of the first visual representation 906 and dates at which the responses were received are located along the horizontal axis 910. The "Trend" tab 902 may further include a selectable indicator 912 permitting the user to show the particular response associated with an individual date. Responsive to user selection of the selectable indicator 912, the "Trend" tab 902 presents one or more windows including the details of the particular response associated with a date. The details may be presented in a list, as shown in FIG. 8, or in any other arrangement. The "Trend" tab 902 may further include a navigation bar 914. Responsive to user translation of the navigation bar 914, the "Trend" tab is configured to proportionately navigate about the first visual representation 906.

As shown in FIG. 9, the "Trend" tab 902 may also include a second visual representation. In particular, FIG. 9 shows a second visual representation 916 of responses to the prompt "Has your weight changed from yesterday?" Responses for this prompt are indicated along the vertical axis 918 of the second visual representation 916 and dates at which the responses were received are located along the horizontal axis 920. The "Trend" tab 902 may further include a selectable indicator 922 permitting the user to show the particular response associated with an individual date and a navigation bar 924 permitting the user to navigate the second graphical representation 916.

In various examples, the "Trend" tab 902 may further include a return indicator 926. Responsive to user selection of the return indicator, the interface 700 may cause the Health Survey Results Review tab 802 of FIG. 8 to be redisplayed.

It is appreciated that, in some examples, the entirety of the user interface screens presented in FIGS. 7-9 may be implemented as a series of prompts processed by a natural language processor, such as the natural language processor 112 described above with reference to FIG. 1. For instance, the prompts described above with reference to the prompt list 706 may be issued by an external medical device as audio or tactile prompts. Verbal responses to these prompts may be processed and the results recorded to configure a health survey for a particular patient.

Example Prompting Processes

Figure 10:
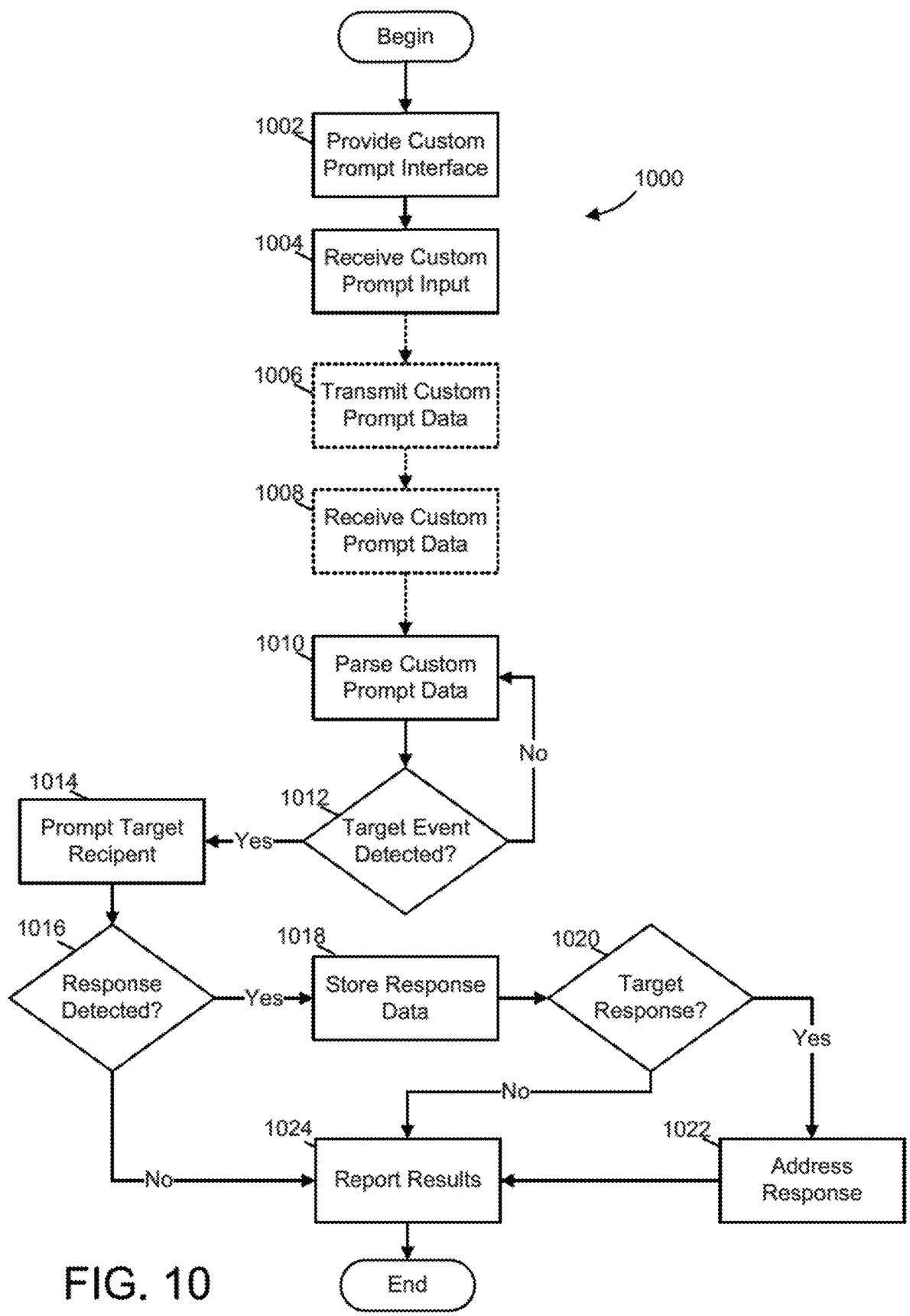
FIG. 10 is a flow diagram of one example of a prompting process.

Various examples implement processes through which an external medical device prompts a target recipient using natural language. These prompts may take the form of questions in a health survey or instructions and training, among other forms. FIG. 10 illustrates one such prompting process 1000 in which a distributed prompting system, such as the distributed prompting system 500 described above with reference to FIG. 5, receives customized prompts and distributes the customized prompts to one or more external medical devices for subsequent output. In this example, the external medical device may be configured in accord with the external medical device 300, the external medical device 400, or another external medical device. Further, the external medical device may include a medical device controller, such as the medical device controller 102 described above with reference to FIG. 1.

As shown in FIG. 10, the prompting process 1000 begins with provision of a custom prompt interface in act 1002. The custom prompt interface may include a variety of user interface elements rendered according to various designs. In some examples, the computer system 520 described above with reference to FIG. 5 renders the custom prompt interface 516. In some examples, the computer system 508 renders the custom prompt interface via a local user interface (e.g., connected via WiFi to a local LAN for access on a computer terminal in the hospital). In some implementations, the custom prompt interface may be disposed on the medical device itself to facilitate local configuration and set-up. In one example where the custom prompt interface is directed to health survey prompts, the custom prompt interface renders a user interface screen in accord with the user interface screens described above with reference to FIGS. 7 through 9. As described above, in some examples, the information presented in these user interface screens is rendered as natural language prompts (e.g., audio prompts or visual prompts in the form of sign language). In some examples, the custom prompt interface provides information regarding selectable health survey prompts. In some examples, the custom prompt interface provides information regarding selectable instruction prompts. In some examples, the custom prompt interface provides information regarding selectable training prompts. In some examples, the custom prompt interface provides user interface elements configured to receive text or other input specifying and selecting new prompts to be transmitted to the external medical device.

In act 1004, the custom prompt interface receives custom prompt input from a user, such as the health care professional 518 or the support technician 504 described above with reference to FIG. 5. This custom prompt input may be in any form detectable by a computer system. Examples of custom prompt input include entered text, one or more selections of user interface elements, and the like. For instance, with reference to FIG. 5, the custom prompt input may include a selection of a check box corresponding to a prompt. In response to receiving the custom prompt input, the custom prompt interface stores data representative of the input in a data store, such as may be implemented, for example, in computer readable memory or computer readable data storage. In some examples, the data representative of the input is stored for subsequent processing as custom prompt data.

In optional act 1006, the custom prompt interface transmits custom prompt data to the external medical device. In cases where the custom prompt data is stored locally, e.g., within a data storage element in the medical device controller, this act 1006 can be skipped. This custom prompt data may include identifiers of previously defined prompts, definitions of new prompts, identifiers of previously defined target events that trigger prompts, definitions of new target events that trigger prompts, identifiers of previously defined responses to be addressed, definitions of new responses to be addressed, identifiers of previously defined actions to be taken in addressing responses, and definitions of new actions to be taken in addressing responses. The transmission of the custom prompt data may be performed using a variety of components that support various protocols, such as via email, FTP, or more specialized transmission techniques. In some examples, the custom prompt data is transmitted to the external medical device as a change to configuration information within a secure update process, such as the update processes described in U.S. Patent Application Publication 2013/0231711, titled "SYSTEMS AND METHODS FOR CONFIGURING A WEARABLE MEDICAL MONITORING AND/OR TREATMENT DEVICE," published Sep. 5, 2013, which is hereby incorporate herein by reference in its entirety.

In optional act 1008, the external medical device receives the custom prompt data and stores the custom prompt data in a data store. In implementations where the custom prompt data is stored locally, this act 1008 can be skipped. In some examples, the external medical device repeatedly executes the act 1008 while executing other acts to ensure that any custom prompt data transmitted by the custom prompt interface is received and stored in the external medical device.

In act 1010, the external medical device parses the custom prompt data to identify target events that trigger one or more prompts. These target events may include any occurrence that is detectable by the external medical device. Examples of target events include presence of target environmental characteristics, presence of target physical conditions of a patient, presence of target operational statuses of the external medical device, presence of target time periods, and the like. In one particular example, the custom prompt data specifies the target time period. In additional examples, the custom prompt data omits the target time period and a default time period is identified.

In act 1012, the external medical device attempts to detect a target event. If the external medical device detects a target event, the external medical device proceeds to act 1014. In the act 1014, the external medical device issues one or more prompts triggered by the target event to one or more target recipients identified within the prompt definition. Also within the act 1014, the external medical device returns to the act 1010 and parses any newly received custom prompt data.

By monitoring for events in the act 1012, the external medical device may issue prompts in the act 1014 upon receipt (e.g., where the event is detection of the readiness of the external medical device to issue the prompt), according to a schedule (e.g., where the event is detection of the current time being within a targeted time period), in response to indications of potential health conditions of a patient as detected by any of the sensors of the external medical device described herein (for example, a cardiac arrhythmia, shortness of breath, garbled speech, or other patient abnormality), in response to maintenance being performed on the external medical device (e.g., wherein the event is detection of a battery, such as the battery 110 described above with reference to FIG. 1, being replaced), or upon detection of other target events. Further, within the act 1012, if the external medical device does not detect a target event, the external medical device returns to the act 1010 and parses any newly received custom prompt data.

The prompts may be delivered as synthesized speech by, for example, converting textual input provided through the custom prompt interface to speech in a language understandable by the patient. For example, a text-to-speech converter may be employed to perform the voice synthesis, e.g., a reproduction of human speech. In this example, the text may be analyzed. The custom prompt may comprise an utterance composed of words and/or phrases, which may be linguistically analyzed for, e.g., phasing, intonation, and duration, to result in an utterance composed of phonemes. Through the analysis of the phonemes, speech wave forms may be generated to output the spoken prompts.

In some examples, the prompts may be delivered by an on-screen animation or illustration of a person performing sign language. As noted above, the custom prompts may be decomposed into words and/or phrases for further conversion to a suitable format for sign language processing (e.g., to output to a patient via American sign language). Divisions are generally made using separators such as punctuation marks and spaces in the text; however, in some implementations divisions may include multiple words, such as a phrase. Once decomposed, individual words and/or phrases may be matched to a database of animations or on-screen illustrations of sign language corresponding to each of the individual words or phrases. Through the analysis of the custom prompt, the corresponding illustrations of sign language or on-screen animations may be displayed to the patient.

In other examples, the prompts may be delivered by a printing device as a tactile output (Braille). As described above, the custom prompts may be decomposed into letters, words, phrases, and/or punctuation for further conversion to a suitable format for tactile language processing (e.g., to output to a patient via Braille). In contrast to reproductions of human speech or illustrations of sign language, custom prompts to be rendered as tactile output may be deconstructed into individual letters and punctuation marks. Once deconstructed, individual letters and punctuation marks are matched to a database of Braille letters and punctuation marks and reassembled to form words, phrases, and sentences. Through analysis and transposition of the custom prompt to Braille, a tactile output may be printed and delivered to a patient who is unable to otherwise hear a speech waveform or see an illustrated animation.

In act 1016, the external medical device attempts to detect a response within a predetermined period of time specified by a configurable parameter. If the external medical device detects a response within the predetermined period of time, the external medical device proceeds to act 1018. If the external medical device does not detect a response within the predetermined period of time, the external medical device proceeds to act 1024.

In act 1018, the external medical device stores data representative of the response in a data store. In act 1020, the external medical device determines whether the response received is a target response to be addressed by the external medical device (e.g., as defined within the custom prompt data). Examples of addressable events include events that indicate a patient is in need of assistance (as detected by any of the sensors of the external medical device described herein) and events that indicate the external medical device is in need of repair or maintenance.

If the external medical device determines that the response is addressable, the external medical device addresses the response in act 1022. In addressing a response, the external medical device may alter a course of treatment (e.g., delay a therapeutic shock or expedite a therapeutic shock), adjust a configurable operational parameter of the external medical device, prompt a third party to take action via a natural language prompt (e.g., call an emergency service and report the event and information regarding the patient, such as location, identity, and vital signs, to the service), or prompt a user to take action via a natural language prompt (e.g., change a battery).

In the act 1024, the external medical device reports the results of the prompting process 1000. FIGS. 8 and 9 illustrate user interface screens provided by the external medical device for this purpose according to some examples.

In some examples, execution of the acts 1006 and 1008 is not required. For instance, where the acts 1002 and 1004 are executed by the external medical device, rather than a distinct computer system, the custom prompt data is stored locally on the external medical device, thereby eliminating the need to execute the acts 1006 and 1008.

Process 1000 depicts one particular sequence of acts in a particular example. The acts included in this process may be performed by, or using, one or more computer systems specially configured as discussed herein. Some acts are optional and, as such, may be omitted in accord with one or more examples. Additionally, the order of acts can be altered, or other acts can be added, without departing from the scope of the systems and methods discussed herein. Furthermore, as discussed above, in at least one example, the acts are performed on a particular, specially configured machine, namely a medical device configured according to the examples disclosed herein.

In some examples, the external medical devices described herein may use custom prompts as part of a physical activity test (e.g., a six minute walk test) administered to the patient. The external medical device may be employed to monitor the gait of the patient while the patient walks. In these examples, the custom prompts may be communicated to guide the patient throughout the physical activity test, ascertain patient conditions prior to, during, and after the test, and provide warnings for emergency conditions occurring during the test. Custom prompts may request, for example, shortness of breath information and fatigue information. Furthermore, warnings may include alerts and instructions to cease the physical activity test because of detected indicators of a cardiac arrest or other health problems. These physical activity tests may include, for example, a six minute walk test as described in U.S. patent application Ser. No. 12/833,173, titled "WEARABLE MEDICAL TREATMENT DEVICE WITH MOTION/POSITION DETECTION," filed Jul. 9, 2010, which is hereby incorporated herein by reference herein in its entirety, and the paper "Guidelines for the Six-Minute Walk Test" published by the American Thoracic Society in March 2002, which is hereby incorporated herein by reference herein in its entirety.

Having thus described several aspects of at least one example of this disclosure, it is to be appreciated various alterations, modifications, and improvements will readily occur to those skilled in the art. Such alterations, modifications, and improvements are intended to be part of this disclosure, and are intended to be within the scope of the disclosure. Accordingly, the foregoing description and drawings are by way of example only.

What is claimed is:

1. An external cardiac monitoring device for providing audio health surveys to a heart failure patient comprising:
   a garment configured to be worn by the heart failure patient, the garment comprising:
   a plurality of electrocardiogram (ECG) electrodes disposed in the garment and configured to couple to the heart failure patient and to acquire ECG signals of the heart failure patient over an extended period of time, and
   a plurality of therapy electrodes disposed in the garment and configured to deliver a therapeutic shock to the heart failure patient;
   a memory; and
   circuitry, configured to communicate with the memory and the plurality of ECG electrodes, and further configured to:
   monitor the ECG signals for a patient abnormality in the heart failure patient;
   receive custom prompt data from a health care provider specifying a customized health care survey for the heart failure patient;
   parse the custom prompt data to identify a target event detectable by the external cardiac monitoring device, a plurality of custom text prompts to be included in the health care survey, the plurality of custom text prompts comprising a plurality of questions regarding the target event, a target response to be addressed by the external cardiac monitoring device, and one or more actions that the external cardiac monitoring device is to perform based upon how the heart failure patient responds to the health care survey, a particular one of the one or more actions being associated with the target response;
   detect a location of the external cardiac monitoring device;
   determine one or more language-based parameters for the patient, the one or more language-based parameters comprising a language associated with the location of the cardiac monitoring device;
   monitor the patient or the device for the target event;
   convert the plurality of questions into an audio representation of the plurality of questions using the one or more language-based parameters comprising the language associated with the location of the cardiac monitoring device;
   responsive to detecting the target event, deliver to the heart failure patient the audio representation of the plurality of questions;
   receive patient responses to the audio representation of the plurality of questions;
   determine that at least one of the patient responses comprises the target response to be addressed by the external cardiac monitoring device as identified from parsing the custom prompt data received from the health care provider;
   perform a predetermined action in response to determining that at least one of the patient responses comprises the target response, wherein the predetermined action comprises adjusting a configurable parameter of the external cardiac monitoring device that defines a course of treatment executed by the external cardiac monitoring device to treat the heart failure patient;
   provide an output report relating to the health care survey, the output report comprising a visual representation of changes in answers provided by the heart failure patient to at least one of the questions over a time period, wherein the visual representation shows answers provided by the heart failure patient over multiple performances of the health care survey; and responsive to detecting, using the plurality of ECG electrodes, a life-threatening arrhythmia, deliver, using the plurality of therapy electrodes, one or more pacing pulses or a defibrillating shock to the patient.

2. The external cardiac monitoring device of claim 1, wherein the external cardiac monitoring device comprises a non-invasive medical device.

3. The external cardiac monitoring device of claim 1, wherein the external cardiac monitoring device comprises an ambulatory medical device capable of and designed for moving with the heart failure patient.

4. The external cardiac monitoring device of claim 1, wherein the external cardiac monitoring device includes components to be continuously worn by the heart failure patient.

5. The external cardiac monitoring device of claim 1, wherein the circuitry includes circuitry to provide a user interface via which the custom prompt data from the health care provider is received.

6. The external cardiac monitoring device of claim 1, wherein the circuitry includes circuitry to:
determine, based on the custom prompt data, a target time period for performing the health care survey according to a schedule; and
record the target time period within the schedule.

7. The external cardiac monitoring device of claim 6, wherein the circuitry includes circuitry to determine the target time period based on an operating mode of the external cardiac monitoring device.

8. The external cardiac monitoring device of claim 7, wherein the circuitry to determine the target time period is configured to determine the target time period as being as soon as possible where the operating mode of the external cardiac monitoring device is set to a health survey mode.

9. The external cardiac monitoring device of claim 6, wherein the custom prompt data specifies the target time period.

10. The external cardiac monitoring device of claim 6, wherein the custom prompt data omits the target time period and the circuitry includes circuitry to store the target time period as a default time period.

11. The external cardiac monitoring device of claim 1, wherein the circuitry includes circuitry to:
record the patient responses;
determine results based on the patient responses; and
provide the results to an external entity via a user interface.

12. The external cardiac monitoring device of claim 6, wherein the target time period includes a reoccurring time period.

13. The external cardiac monitoring device of claim 1, wherein the circuitry includes circuitry to:
output an audio representation of at least one of the patient responses.

14. The external cardiac monitoring device of claim 1, further comprising a cross-reference stored in the memory, the cross-reference including associations between response types and addresses for target recipients,
wherein the circuitry includes circuitry
to identify at least one response type of a particular one of the patient responses,
to identify at least one address for at least one target recipient from the cross-reference using the at least one response type, and
to transmit at least one notification to the at least one target recipient.

15. The external cardiac monitoring device of claim 1, further comprising a cross-reference stored in the memory, the cross-reference including associations between response types and addresses for target recipients,
wherein the circuitry includes circuitry
to identify at least one response type of a particular one of the patient responses,
to identify at least one address for at least one target recipient from the cross-reference using the at least one response type, and
to transmit at least one notification to the at least one target recipient,
the at least one target recipient including a device associated with at least one of the health care provider, a support provider, or a care taker and
the at least one notification including a natural language representation of at least one of a name of the heart failure patient, a location of the heart failure patient, a condition of the heart failure patient, or at least one of the patient responses.

16. The external cardiac monitoring device of claim 1, further comprising a cross-reference stored in the memory, the cross-reference including associations between response types and priorities for subsequent actions,
wherein the circuitry includes circuitry
to identify at least one response type of a particular one of the patient responses,
to identify at least one priority from the cross-reference using the at least one response type, and
to transmit at least one notification with the at least one priority.

17. The external cardiac monitoring device of claim 1, wherein the circuitry is further configured to detect one or more health indicators in the heart failure patient, and the output report comprises at least one patient health trend that indicates a change in speech of the heart failure patient.

18. The external cardiac monitoring device of claim 17, wherein the one or more health indicators comprise at least one of shortness of breath, fatigue, or an emergency condition.

19. The external cardiac monitoring device of claim 1, wherein the circuitry is configured to alert the heart failure patient of one or more health indicators by providing at least one of a request to provide shortness of breath information or a request to provide fatigue information.

20. The external cardiac monitoring device of claim 1, wherein the one or more actions that the external cardiac monitoring device is to perform comprises at least one of requesting additional information from the heart failure patient, providing additional training information to the heart failure patient, or requesting emergency assistance on behalf of the heart failure patient.

21. The external cardiac monitoring device of claim 1, wherein the visual representation includes a selectable indicator that, when selected, causes an answer that was provided by the heart failure patient on a particular date to be displayed.

22. The external cardiac monitoring device of claim 1, wherein the visual representation includes a navigation bar that, when manipulated, causes the visual representation to display answers provided by the heart failure patient during a particular portion of the time period.

23. The external cardiac monitoring device of claim 1, wherein the circuitry is configured to
deliver to the heart failure patient the audio representation of the plurality of questions in association with a physical activity test selected by the health care provider for the heart failure patient,
wherein the plurality of custom text prompts further comprise a prompt requesting that the heart failure patient perform the physical activity test,
wherein the plurality of questions includes a first plurality of questions scheduled for delivery to the heart failure patient before the physical activity test,
wherein the plurality of questions includes a second plurality of questions scheduled for delivery to the heart failure patient after the physical activity test, and
wherein delivering to the heart failure patient the audio representation of the plurality of questions in association with the physical activity test comprises delivering an audio representation of the first plurality of questions before the physical activity test and delivering an audio representation of the second plurality of questions after the physical activity test;
detect one or more health indicators in the heart failure patient during performance of the physical activity test; and
alert the heart failure patient of the one or more health indicators during the physical activity test by one or more of instructing the heart failure patient to slow down during the physical activity test based upon the one or more health indicators or instructing the heart failure patient to stop the physical activity test based upon the one or more health indicators.

24. The external cardiac monitoring device of claim 23, wherein the physical activity test comprises a six minute walk test.

25. The external cardiac monitoring device of claim 1, wherein adjusting the configurable parameter causes administration of the therapeutic shock to be delayed or expedited.

26. The external cardiac monitoring device of claim 1, wherein the one or more actions that the external cardiac monitoring device is to perform comprises prompting a user, via a natural language prompt, to call an emergency service.

27. The external cardiac monitoring device of claim 1, wherein the one or more actions that the external cardiac monitoring device is to perform comprises prompting a user to change a battery of the external cardiac monitoring device.

* * * * *